(12) United States Patent
Miller et al.

(10) Patent No.: US 8,002,743 B2
(45) Date of Patent: Aug. 23, 2011

(54) SYSTEMS AND METHODS FOR NEEDLE ACCESS TO AN INTERVERTEBRAL DISC

(75) Inventors: David Miller, Cupertino, CA (US);
Michael Smith, San Jose, CA (US);
Steve Mouw, Santa Clara, CA (US);
Erika Palmer, Menlo Park, CA (US)

(73) Assignee: Kyphon SARL, Neuchatel (CH)

( * ) Notice: Subject to any disclaimer, the term of this patent is extended or adjusted under 35 U.S.C. 154(b) by 33 days.

(21) Appl. No.: 11/764,085

(22) Filed: Jun. 15, 2007

(65) Prior Publication Data
US 2008/0312636 A1  Dec. 18, 2008

(51) Int. Cl.
*A61M 29/00* (2006.01)
*A61M 1/00* (2006.01)
*A61M 5/00* (2006.01)

(52) U.S. Cl. ............ 604/99.03; 604/129; 604/247

(58) Field of Classification Search ........ 604/96.01, 604/99.01–99.03, 118, 129, 167.03, 167.05, 604/236–238, 247–248; 138/159
See application file for complete search history.

(56) References Cited

U.S. PATENT DOCUMENTS

| | | | |
|---|---|---|---|
| 3,467,101 A * | 9/1969 | Raible et al. .......... 606/194 |
| 3,780,604 A * | 12/1973 | Wood et al. .......... 81/64 |
| 4,758,224 A * | 7/1988 | Siposs .......... 604/119 |
| 4,798,590 A * | 1/1989 | O'Leary et al. .......... 604/153 |
| 4,850,953 A * | 7/1989 | Haber et al. .......... 600/32 |
| 4,949,716 A | 8/1990 | Chenoweth |
| 5,061,239 A * | 10/1991 | Shiels .......... 604/26 |
| 5,085,631 A | 2/1992 | Leighton |
| 5,423,741 A * | 6/1995 | Frank .......... 604/26 |
| 5,573,519 A | 11/1996 | Zohmann |
| 5,591,129 A * | 1/1997 | Shoup et al. .......... 604/103.1 |
| 6,245,044 B1 | 6/2001 | Daw et al. |
| 6,613,066 B1 * | 9/2003 | Fukaya et al. .......... 606/192 |
| 6,929,640 B1 | 8/2005 | Underwood et al. |
| 7,004,961 B2 | 2/2006 | Wong et al. |

(Continued)

FOREIGN PATENT DOCUMENTS

WO  WO 2005/102440  11/2005

(Continued)

OTHER PUBLICATIONS

U.S. Appl. No. 60/826,472, filed Sep. 21, 2006, inventor: David Miller.

(Continued)

*Primary Examiner* — Kevin C Sirmons
*Assistant Examiner* — Bradley J Osinski
(74) *Attorney, Agent, or Firm* — Haynes and Boone, LLP

(57) ABSTRACT

A catheter with a balloon anchor may be sized to fit through an inner needle and introduced into the patient through the needle. The inner needle may comprise an atraumatic needle with a side port and/or a blunt tip. The catheter may include a radiopaque coil disposed over the distal portion of the catheter body to assist with catheter placement when viewed with fluoroscopy and/or x-ray. The distal portion of the catheter can be very flexible. A balloon inflation tube may terminate proximal to a proximal end of the expandable balloon anchor such that the distal portion of catheter can be flexible. This termination of the inflation tube may also position the inflation tube away from the annulus and nerve roots, so as to avoid irritation of the annulus and rubbing of the nerve roots that may potentially obscure FAD test results.

4 Claims, 24 Drawing Sheets

U.S. PATENT DOCUMENTS

| | | | |
|---|---|---|---|
| 7,056,274 B2 * | 6/2006 | Apple et al. | 600/3 |
| 7,069,087 B2 | 6/2006 | Sharkey et al. | |
| 7,400,930 B2 | 7/2008 | Sharkey et al. | |
| 2004/0193145 A1 * | 9/2004 | Raudabough et al. | 606/1 |
| 2005/0043808 A1 * | 2/2005 | Felt et al. | 623/20.14 |
| 2005/0234425 A1 | 10/2005 | Miller et al. | |
| 2006/0095059 A1 | 5/2006 | Bleich et al. | |
| 2006/0149136 A1 | 7/2006 | Seto et al. | |
| 2006/0149218 A1 * | 7/2006 | Slater et al. | 604/509 |
| 2007/0038300 A1 * | 2/2007 | Bao et al. | 623/17.12 |
| 2007/0135768 A1 | 6/2007 | Carlsen | |
| 2008/0200871 A1 * | 8/2008 | Slater et al. | 604/96.01 |

FOREIGN PATENT DOCUMENTS

| | | | |
|---|---|---|---|
| WO | 2006130491 A2 | 12/2006 | |

OTHER PUBLICATIONS

Pajunk GMBH, "IntraLong-Set with Special-Sprotte Cannula," Apr. 2004, www.pajunk.com, 4 pages.

Havel's Incorporated, "Atraumatic Sprotte Spinal Needle," www.havels.com, 2 pages, Nov. 2006.

European Patent Office, "Notification of Transmittal of the International Search Report and The Written Opinion of the International Searching Authority, or the Declaration," for PCT/US2008/066699, mailed Sep. 30, 2008, 15 pages.

* cited by examiner

SYSTEMS AND METHODS FOR NEEDLE ACCESS TO AN INTERVERTEBRAL DISC

CROSS-REFERENCES TO RELATED APPLICATIONS

The subject matter of the present application is related to but does not claim the benefit of the following commonly assigned and concurrently filed U.S. patent application Ser. Nos. 11/764,029, filed on Jun. 15, 2007, entitled "DEVICE AND METHODS FOR INTRODUCING A CATHETER INTO AN INTERVERTEBRAL DISC"; 11/764,050, filed on Jun. 15, 2007, entitled "SYSTEMS AND METHODS FOR NEEDLE ACCESS TO INTERVERTEBRAL DISC"; and 11/764,067, filed on Jun. 15, 2007, entitled "SYSTEMS AND METHODS FOR NEEDLE ACCESS TO INTERVERTEBRAL DISC", the full disclosures of which are hereby incorporated by reference.

BACKGROUND OF THE INVENTION

The present invention generally relates to medical devices and methods. More particularly, the present invention relates to devices and methods for diagnosing and/or treating spinal pain.

Back pain takes an enormous toll on the health and productivity of people around the world. According to the American Academy of Orthopedic Surgeons, approximately 80 percent of Americans will experience back pain at some time in their life. In just the year 2000, approximately 26 million visits were made to physicians' offices due to back problems in the United States.

In at least some instances, surgical prostheses can be used to relieve back pain. Many of these prosthesis relieve pressure and/or irritation of nerve roots near the vertebral joints. Such treatments can be effective when the source of pain can be localized to a specific inter-vertebral joint and/or disc.

Unfortunately, back pain can be difficult and invasive to accurately diagnose in an effective manner that determines where the pain originates. Axial pain can be caused by disc failure that results in compression of nerves. "Discogenic pain," for example, is a type of spinal pain originating in one or more intervertebral discs (soft tissue structures between vertebrae of the spine). The physical examination and complaints of the patient may merely provide general clues as to the cause and general location of the pain.

One approach to determine the source of back pain, can be to perform provocative discography. This procedure can include penetrating the patient's skin and injecting a contrast agent into the disc. The disc can be imaged with fluoroscopy, radiographs, CT scans, or the like with the aid of the contrast agent. Alternatively, a new technique referred to as Functional Anesthetic Discography (FAD) has been developed wherein the disc can be further evaluated with functional tests in which the patient assumes a painful position and the disc is injected with an analgesic or similar substance to determine if the pain diminishes in response to the injection into the disc.

Placement of the spinal needles to test the discs may require skill and time on the clinician's part and can be painful to the patient, even when good technique is used. In some instances, provocative discography may use two needles for each disc. As the patient may have more that one disc that may be a possible source of back pain, each of these suspected discs may be tested to determine which, if any, of the discs is the source of the patient's pain. The testing of multiple discs, for example three discs, can be time consuming and may result in multiple injections for the patient, each of which can be painful. Invasive tearing of tissues, for example associated with conventional needles and the like, may cause tissue trauma and delay recovery in some patients. In addition, some catheters and needles may potentially rub against nerve roots, such that the patient experiences pain, and in some instances may obscure test results.

For these reasons, it would be desirable to provide apparatus and methods for facilitating the diagnosis and treatment of spinal pain. It would be particularly desirable if such methods and apparatus were less invasive and painful than current methods and apparatus, and assured reliable determination of the source of patient pain, ideally while allowing the clinician flexibility with respect to which approach is used in a manner that accommodates patient variability.

Related devices and methods are disclosed in U.S. Patent Publication No. 2005/0234425 describes a Functional Anesthetic Discography (FAD) catheter, the full disclosure of which is incorporated herein by reference. Additional art that may be relevant includes U.S. application Ser. Nos. 11/021,786 and 60/826,472, the full disclosures of which are incorporated herein by reference, and International Publication No. WO 2005/102440.

SUMMARY OF THE INVENTION

Embodiments of the present invention may provide less invasive and safer systems and methods to access, diagnose, and treat spinal pain. A catheter, such as an FAD catheter with a balloon anchor, may be sized to fit through a relatively small inner needle, for example a 0.9 mm or smaller needle. Optionally, the clinician may use a needle that has already been placed, thereby benefiting from a pre-existing access port and decreasing the invasiveness of the procedure. In specific embodiments, an atraumatic needle can be used to introduce the catheter into the interior of the disc of the patient. Such atraumatic needles may reduce the incidence of complications and trauma to the penetrated tissue, for example leakage through a penetrated disc annulus, or impaired healing from the trauma imparted on the annulus by passing the needles. The atraumatic needle may comprise a side port and blunt tip to minimize tissue damage. The tip will usually comprise an integrated sharpened end, but could alternatively comprise a radiofrequency electrode (capable of applying cutting current), a removably or separately formed sharpened end, or the like. The catheter may include a radiopaque marker, for example a coil, disposed over the distal portion of the catheter body to assist with catheter placement when viewed with fluoroscopy and/or x-ray. In addition to making the catheter visible with fluoroscopy and/or x-ray, the coil may be very flexible, such that the distal portion of the catheter can be very flexible. The coil along the distal portion of the catheter may provide improved safety, as the coil may retain the distal catheter portion in the unlikely, yet potentially serious, situation in which the distal tip of the catheter breaks. In some embodiments, an inflation tube may terminate proximal to a proximal end of the expandable balloon anchor. This termination of the inflation tube, along with the flexible coil, may permit the distal portion of catheter to be flexible. This termination of the inflation tube may also position the inflation tube away from the annulus and nerve roots, so as to avoid irritation of the annulus and rubbing of the nerve roots that may potentially obscure FAD test results.

In a first aspect, embodiments of the present invention provide a method for positioning a catheter in an interior of an intervertebral disc. The method comprises percutaneously advancing a first needle through a skin toward the intervertebral disc. A second needle may be advanced through a lumen of the first needle to penetrate through a surface of the intervertebral disc into the interior of the disc. A catheter may be advanced through a lumen of the second needle into the interior of the disc.

In many embodiments, the first needle may be advanced with a stylet or obturator in its lumen, the stylet or obturator may be removed after the first needle has reached the surface location. The first needle may have an inner diameter of no more than 1.7 mm and a length in the range from 3 cm to 26 cm.

In some embodiments, the second needle can be advanced with a stylet or obturator in its lumen, the stylet or obturator can be removed after the second needle has reached the interior of the disc. The second needle may have an outer diameter no greater than 1.5 mm and an inner diameter of at least 0.38 mm. The catheter may have an outside cross sectional size no greater than 1.5 mm and a length in the range from 30 cm to 62 cm.

In many embodiments indicia on a proximal portion of the catheter may be observed as the catheter is advanced through the lumen of the second needle. The indicia may indicate a position of the catheter relative to a distal end of the second needle so that a user will know when the catheter has passed from the second needle into the interior of the disc. The indicia may comprise a scale formed on the exterior of a proximal portion of the catheter. In specific embodiments, the indicia may comprise a color change on the catheter.

In some embodiments, the catheter can be advanced through a side port of the second needle to advance the catheter into the interior of the disc. The catheter may be advanced into the interior of the disc through the side port at a deflection angle of about 5 to 35 degrees from the second needle. The second needle can be retracted such that the catheter slides along a side port of the second needle and a distal tip of the catheter remains in the interior of the disc. In specific embodiments, the first needle can be retracted to retract the second needle and slide the side port along the catheter.

In some embodiments, an expandable balloon can be inflated to anchor the catheter in the disc interior after the second needle has been retracted.

In another aspect, embodiments of the present invention provide a system for positioning a catheter in an intervertebral disc of a patient in which the intervertebral disc has an annulus and a nucleus. The system comprises a needle sized to extend through a skin of the patient and through the annulus into the nucleus. The needle comprises an inner lumen and a closed distal tip. The system also comprises a catheter sized to fit inside the lumen of the needle and extend into the nucleus.

In some embodiments, the catheter comprises a balloon anchor sized to pass through the lumen into the nucleus.

In many embodiments, the distal tip of the needle comprises a tapered profile, and the distal tip of the needle may comprise an atraumatic needle tip. For example, the closed distal tip of the needle may comprise a side port, and the lumen may extend to the side port. The needle may be adapted to slide along the catheter and out the side port while the atraumatic needle tip is withdrawn through the annulus. Thus, the catheter can remain in the nucleus after the atraumatic needle has been withdrawn.

In some embodiments, the system comprises an outer needle to penetrate a skin of the patient. The outer needle may comprise a lumen, and the needle can be sized to fit inside the lumen of outer needle.

In some embodiments, the catheter comprises a bend radius from about 5 to 15 mm. The side port can be adapted to pass the catheter with the bend radius from about 5 to 15 mm so as to slide the catheter through the side port while the needle is retracted through the annulus.

In specific embodiments, the atraumatic needle tip comprises a Special Sprotte needle tip, and the needle comprises an outside diameter no more than about 0.92 mm.

In many embodiments, the catheter comprises a balloon anchor sized to pass through the side port.

In some embodiments, the system comprises an adapter that connects to a lumen of the catheter, and a wing nut to tighten the adapter on the catheter lumen. The wing nut may comprise a slot sized to pass the lumen when the wing nut is removed from the adapter.

In another aspect, embodiments of the present invention provide a method of positioning a catheter in an intervertebral disc of a patient in which the intervertebral disc has an annulus and a nucleus. The method comprises advancing a needle to penetrate through a surface of the intervertebral disc into the interior of the disc. A catheter is advanced through a lumen of the needle into the interior of the disc.

In many embodiments, a balloon is inflated to anchor the catheter in the disc.

In another aspect, embodiments of the present invention provide a system for positioning a catheter in an interior of an intervertebral disc. The system may comprise a first needle capable of receiving a first removable stylet for establishing a percutaneous path through a skin towards the intervertebral disc in a patient's body. The system may also comprise a second needle that is capable of receiving a second removable stylet. The second needle can be sized to advance through a lumen of the first needle, after the first removable stylet has been removed. The second needle can be advanced into the interior of the intervertebral disc. The system may further comprise a catheter that is sized for introduction through a lumen of the second needle after the second stylet has been withdrawn.

In many embodiments, the first needle may include a removable stylet, obturator or trocar to inhibit coring. The first needle may have an inner diameter of no more than 1.7 mm and a length in the range from 3 cm to 20 cm. The second needle may include a removable stylet or obturator to inhibit coring. In specific embodiments, the second needle may have an outer diameter no greater than 1.5 mm, an inner diameter of at least 0.38 mm, and a length in a range from 10 cm to 30 cm. The catheter may have an outside cross sectional size no greater than 1.5 mm and a length in the range from 30 cm to 62 cm.

In some embodiments, the catheter may comprise indicia over a proximal portion thereof. The indicia may indicate the position of the distal end of the catheter relative to the distal end of the second needle. The indicia may comprise a scale formed printed or etched on a surface of the catheter. In specific embodiments, the indicia may comprise a color change on the catheter.

In many embodiments, the second needle may comprise an atraumatic needle adapted to minimize tissue damage with at least one of an atraumatic tip or a side port. The second needle comprises a ramp near the side port to pass the catheter through the side port at a deflection angle of about 5 to 35 degrees from the second needle. In specific embodiments, the second needle may comprise a Sprotte needle. The side port may be capable of sliding along the catheter such that the catheter remains near the disc when the second needle is retracted. The catheter may comprise an expandable balloon sized to pass through the side port.

In specific embodiments, at least one of the first needle or the second needle, or a component of one of the needles, may comprise tungsten, rhenium, molybdenum, tantalum, palladium, cobalt-chromium, tungsten-rhenium, tungsten-carbide or molybdenum-rhenium.

In a further aspect, embodiments of the present invention provide a catheter for accessing an intervertebral disc. The catheter may comprise an elongate flexible catheter body having a proximal portion, a distal portion, and at least one lumen for introducing substances. The catheter may also comprise an inflatable anchoring balloon on the distal portion of the catheter body. A radiopaque coil may be disposed over or through at least a part of the distal portion of the elongate flexible catheter body.

In many embodiments, an injection tube may extend from the proximal portion to or near a distal tip of the catheter body. An inflation tube may extend from the proximal portion to or near the distal portion of the catheter body. The radiopaque coil can be disposed over a distal portion of the injection tube that passes through the inflatable anchoring balloon. The radiopaque coil may extend from a distal tip of the injection tube to a proximal portion of the catheter body.

In some embodiments, the catheter body may comprise a polymeric tube having a central passage which receives the inflation tube and the injection tube. The inflation tube may comprise a metal tube, and the injection tube may comprise a metal tube.

In specific embodiments, the catheter body may have an outside diameter capable of passing through a lumen of a 0.9 mm needle.

In another aspect, embodiments of the present invention may provide a catheter for accessing an intervertebral disc. The catheter may comprise an elongate flexible catheter body having a proximal portion, a distal portion, and at least one lumen for introducing substances. The catheter may also comprise an inflation tube in the elongate body, and an anchoring balloon comprising an inflatable portion disposed on the distal portion of the catheter body. The inflation tube may have a distal end, which terminates proximal to the inflatable portion of the balloon.

In specific embodiments, the distal end of the inflation tube may lie about 5.5 mm proximally of a distal tip of the catheter body.

In many embodiments, the catheter may comprise an injection tube in the elongate body that extends distally past the distal end of the inflation tube and terminate near a distal tip of the catheter body. The injection tube may extend distally beyond a distal end of the anchoring balloon by a distance of at least 2 mm. The portion of the catheter body distal to the distal end of the inflation tube may be more flexible than the portion proximal to the distal end.

In some embodiments, the catheter body may comprise a polymeric tube that has a central passage which receives the inflation tube and the injection tube. The inflation tube may comprise a metal tube, and the injection tube may comprise a metal tube.

In specific embodiments, the catheter body may be configured to pass through the lumen of a 0.9 mm needle.

In specific embodiments, at least one of the coil, the injection tube or the inflation tube comprises comprise tungsten, rhenium, molybdenum, tantalum, palladium, cobalt-chromium, tungsten-rhenium, tungsten-carbide or molybdenum-rhenium.

In another aspect, embodiments of the present invention may provide a catheter for accessing an intervertebral disc. The catheter may comprise an elongate flexible catheter body having a proximal portion, a distal portion, and at least one lumen. The catheter may also comprise an inflatable anchoring balloon on the distal portion of the catheter body, and an injection tube may extend through the at least one lumen from the proximal portion to a distal tip of the catheter body. An inflation tube may extend through the at least one lumen from the proximal portion to the distal portion of the catheter body. At least one of the inflation tube and the injection tube may be coated and/or treated over at least a part of the proximal portion to inhibit fatigue fracturing.

In many embodiments, the at least one tube of the catheter may be coated with a polymer. The polymer may comprise at least one of poly(aryl ether ether ketone), polyethylene terephthalate, polyetherimide, nylon, a filled or ribbed blend, or a combination thereof.

In some embodiments, the at least one tube may be composed of a metal and annealed to improve metal fatigue characteristics. Both the inflation tube and the injection tube can be coated and/or treated to inhibit fatigue fracturing.

In many embodiments, the catheter body may comprise a polymeric tube having a central passage which receives the inflation tube and the injection tube. The catheter body may be reinforced with a metal or polymer.

In specific embodiments, the catheter body may an outside diameter capable of passing through a lumen of a 0.9 mm needle.

In another aspect, embodiments of the invention provide a catheter for accessing an intervertebral disc. The catheter comprises an elongate flexible catheter body having a proximal portion, a distal portion, and at least one lumen for introducing substances. The catheter may also comprise an inflatable anchoring balloon on the distal portion of the catheter body. An injection tube may extend from the proximal portion to a distal tip of the catheter body, and an inflation tube may extend from the proximal portion to the distal portion of the catheter body. At least one of the injection tube and the inflation tube may be marked for identification, for example to allow the clinician to distinguish easily among the tubes.

In many embodiments, the at least one tube is marked with a color. The at least one tube may have a terminal connector which is marked. For example, the terminal connector may be marked with a color.

The catheter body may comprise a polymeric tube having a central passage which receives the inflation tube and the injection tube. The inflation tube may comprise a metal tube, and the injection tube may comprise a metal tube. In specific embodiments, the catheter body may have an outside diameter capable of passing through a lumen of a 0.9 mm needle.

In many embodiments a system comprises the catheter for accessing the intervertebral disc as described above. The system may also comprise a balloon inflation source. The balloon inflation source may have a connector which is marked similarly to the inflation tube. The system may also comprise an injection source, and the injection source may have a connector which is marked similarly to the injection tube.

In another aspect, embodiments of the present invention provide a catheter for accessing an intervertebral disc. The catheter may comprise an elongate flexible catheter body that has a proximal portion, a distal portion, and at least one lumen for introducing substances. The catheter may also comprise an inflatable anchoring balloon on the distal portion of the catheter body. An inflation tube or lumen may have an inlet and an outlet and defining an inflation path. The outlet can be connected to deliver an inflation medium via the inflation path under pressure to the balloon. A pressure-relief structure can be connected or connectable in the balloon inflation path to vent the inflation medium if the pressure exceeds a predetermined amount, such that over inflation and rupture of the balloon can be prevented.

In many embodiments, the catheter may comprise an isolation valve in the inflation tube or lumen so that the balloon inflation path can be closed after the balloon is inflated. In some embodiments, the pressure relief structure may be positioned upstream of the isolation valve so that pressure can vent while the inflation medium is being delivered but not after the isolation valve is closed. In additional embodiments, the pressure relief structure may be downstream of the isolation valve so that pressure can vent even after the valve is closed.

In some embodiments, the pressure relief structure may comprise a part of the isolation valve, and the pressure relief structure and the isolation valve may be parts of an inflation syringe.

In many embodiments, the catheter body may comprise a polymeric tube having a central passage which receives the inflation tube and an injection tube. The inflation tube may comprise a metal tube, and the injection tube may comprise a metal tube. In specific embodiments, the catheter body may have an outside diameter capable of passing through the lumen of a 0.9 mm needle. In some embodiments, the predetermined amount may comprise a range from about 680 kPa to about 1620 kPa.

In another aspect, embodiments of the present invention provide a catheter for accessing an intervertebral disc. The catheter may comprise an elongate flexible catheter body having a proximal portion, a distal portion, and at least one lumen for introducing substances. The catheter may also comprise an inflatable anchoring balloon on the distal portion of the catheter body. An injection tube may extend from the proximal portion to a distal tip of the catheter body. An inflation tube may extend from the proximal portion to the distal portion of the catheter body. A one-way valve may be attached to at least one of the injection tube or the inflation tube, such that the one-way valve may avoid the backflow of substances through the catheter, for example during inflation or injection at high pressure. The one-way valve may also help to retain pressure in the balloon and make it easier for the clinician to close the stopcock valve.

In many embodiments, the one-way valve may be attached to the inflation tube to hold pressure after the balloon has been inflated. The one-way valve can be attached to the injection tube to inhibit leakage of substances after they have been injected. The catheter body may comprise a polymeric tube having a central passage which receives the inflation tube and the injection tube. The inflation tube may comprise a metal tube, and the injection tube may comprise a metal tube. In some embodiments, at least one of the injection tube or the inflation tube comprises tungsten, rhenium, molybdenum, tantalum, palladium, cobalt-chromium, tungsten-rhenium, tungsten-carbide or molybdenum-rhenium. In specific embodiments, the catheter body may have an outside cross sectional size capable of passing through the lumen of a 0.9 mm needle.

DETAILED DESCRIPTION OF THE INVENTION

Figure 1A:
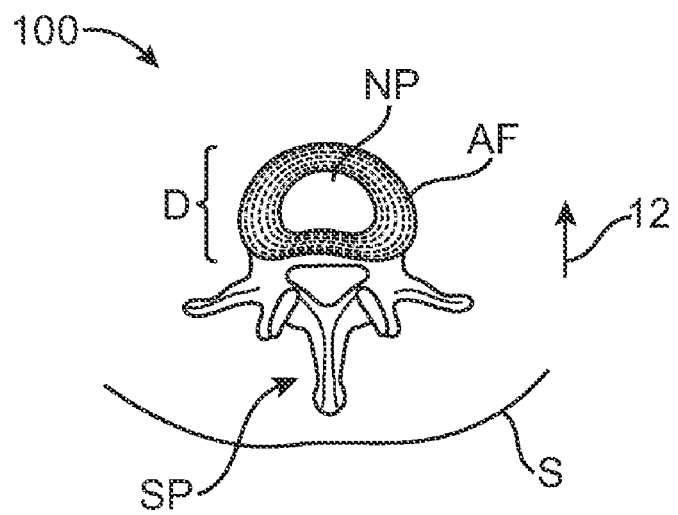
FIG. 1A shows a schematic illustration of a spinal cross section, according to embodiments of the present invention.

Referring now to FIG. 1A, relevant structures are shown of a spinal cross section 10 of a patient, according to embodiments of the present invention. Spinal cross section 10 includes a intervertebral disc D. Intervertebral disc D comprises an annulus fibrosis AF, or annulus, that surrounds a nucleus pulposus NP, or nucleus. A spinous process SP is located near disc D. An arrow 12 points to the anterior of the patient. A skin S of the patient is located posterior to the spinous process SP.

Figure 1B:
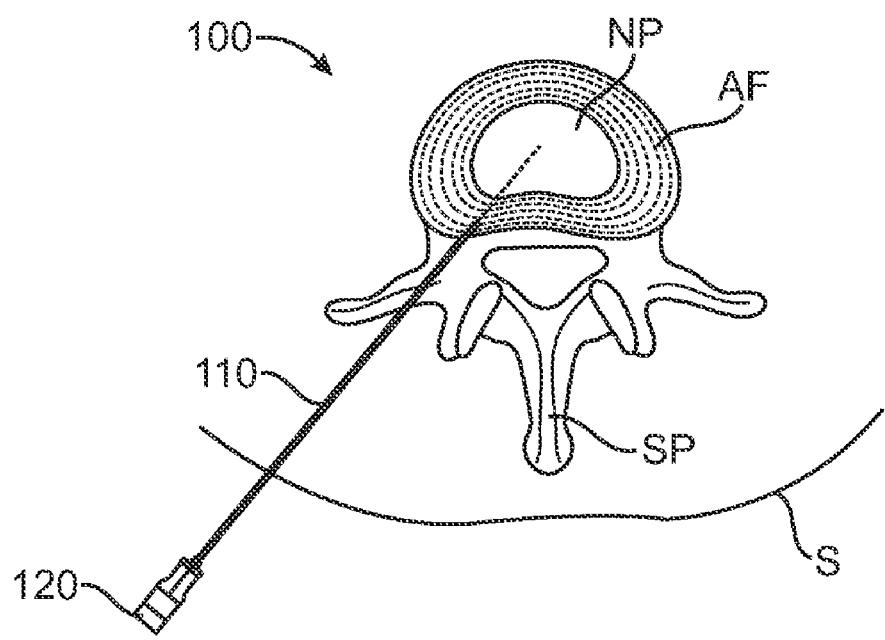
FIGS. 1B to 1D show a FAD placement procedure, according to embodiments of the present invention.
Figure 1C:
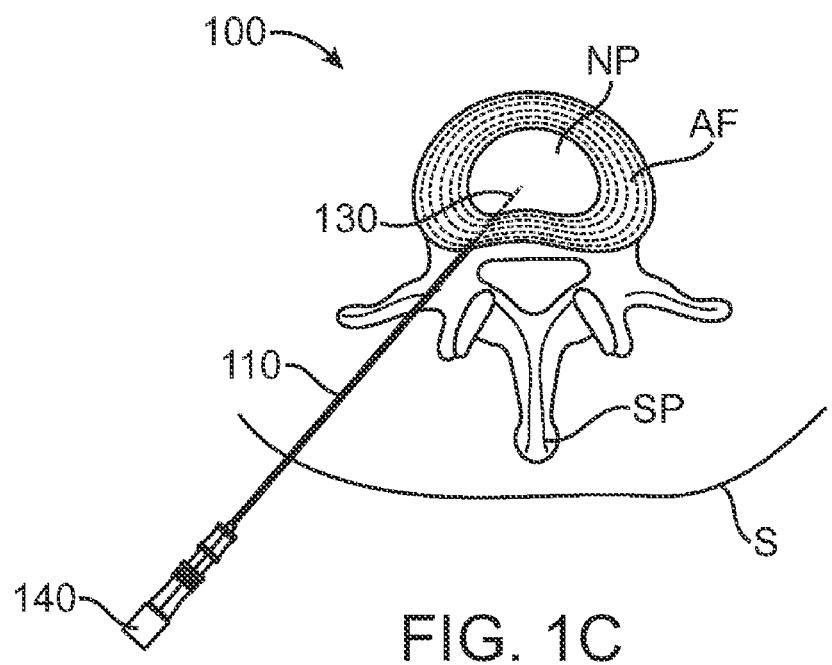
Figure 1D:
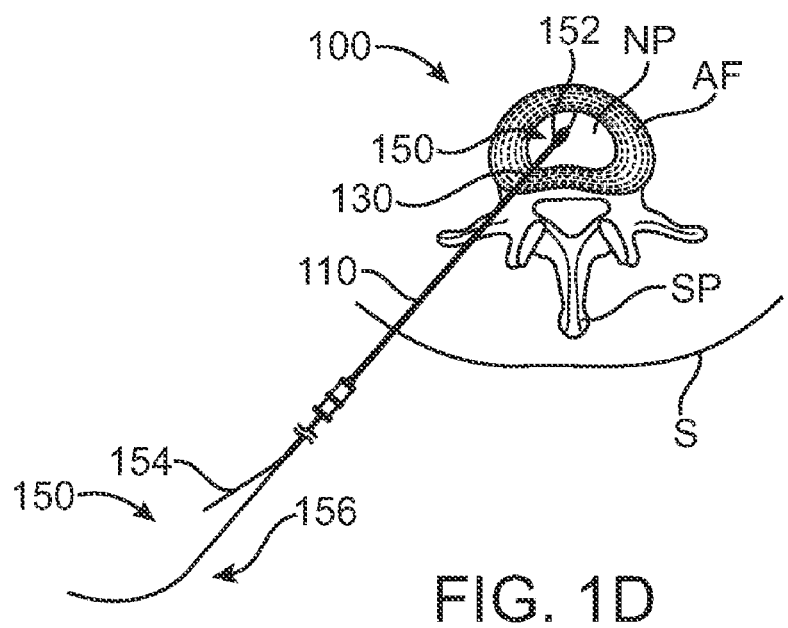

Referring now to FIGS. 1B to 1D, a FAD placement procedure 100 is shown, according to embodiments of the present invention. FIG. 1B shows placement of an outer needle 110. Outer needle 110 can be placed through skin S while an outer needle stylet 120 is positioned inside outer needle 110. Outer needle 110 may comprise a Discyphor outer needle, for example a Discyphor Direct™ needle, available from Kyphon, Inc. of Sunnyvale, Calif. Outer needle 110 may be placed using fluoroscopic guidance to position the needle via a posterolateral approach. In some embodiments, outer needle 110 may be placed using the same approach and placement as needles used for a standard provocative discography. In some embodiments, outer needle 110 may be placed so as to extend to the annulus fibrosis of disc D, for example into the annulus fibrosis as shown in FIG. 1B. In some embodiments needle 110 can be inserted through the annulus into nucleus pulposus NP. Once outer needle 110 is in position, stylet 120 may be removed.

FIG. 1C shows placement of an inner needle 130. Inner needle 130 and an inner needle stylet 140 may be placed inside outer needle 110. Under fluoroscopic guidance, inner needle 130 can be advanced through the outer needle 110, through annulus fibrosis AF and into nucleus pulposus NP of the disc. Stylet 140 of inner needle 130 can be removed after the needle is properly positioned into nucleus pulposus NP of the disc.

FIG. 1D shows advancement of a catheter 150 through inner needle 130 into the disc. While advancing catheter 150, fluoroscopy may be used periodically to ensure that inner needle 130 remains near the center of nucleus pulposus NP and that inner needle 130 does not move beyond this position. Advancement of catheter 150 may pause when slight resistance is felt as the distal tip of catheter 150 approaches an exit ramp of the inner needle 130, described herein below in detail. A radiopaque marker, which marks the center of a balloon 152, may be used to gauge the position of the balloon relative to the annulus. Additionally, location may be confirmed by the color coded markers on the catheter, described herein below in detail. Catheter 150 may comprise a balloon inflation lumen 154 and an injection lumen 156.

After the tip of the catheter is properly positioned, the outer needle and inner needle may be removed simultaneously using, for example, an over the wire technique, while the catheter lies in the nucleus of the disc. The outer needle wing may be pulled back to ensure both needles are removed simultaneously. A Tuohy Borst subassembly may be attached with a blue wing nut to the balloon inflation lumen on the catheter. A radiopaque contrast agent, for example 1.5 cc of a 100% radiopaque contrast agent, may be drawn into a 3 cc syringe with an attached pressure relief valve as described herein below. The 3 cc syringe with the attached pressure relief valve can be attached to a stopcock by tightening and/or turning a Luer-lock hub of the pressure relief valve. The radiopaque contrast can be injected through the inflation lumen to expand the balloon.

Figure 1E:
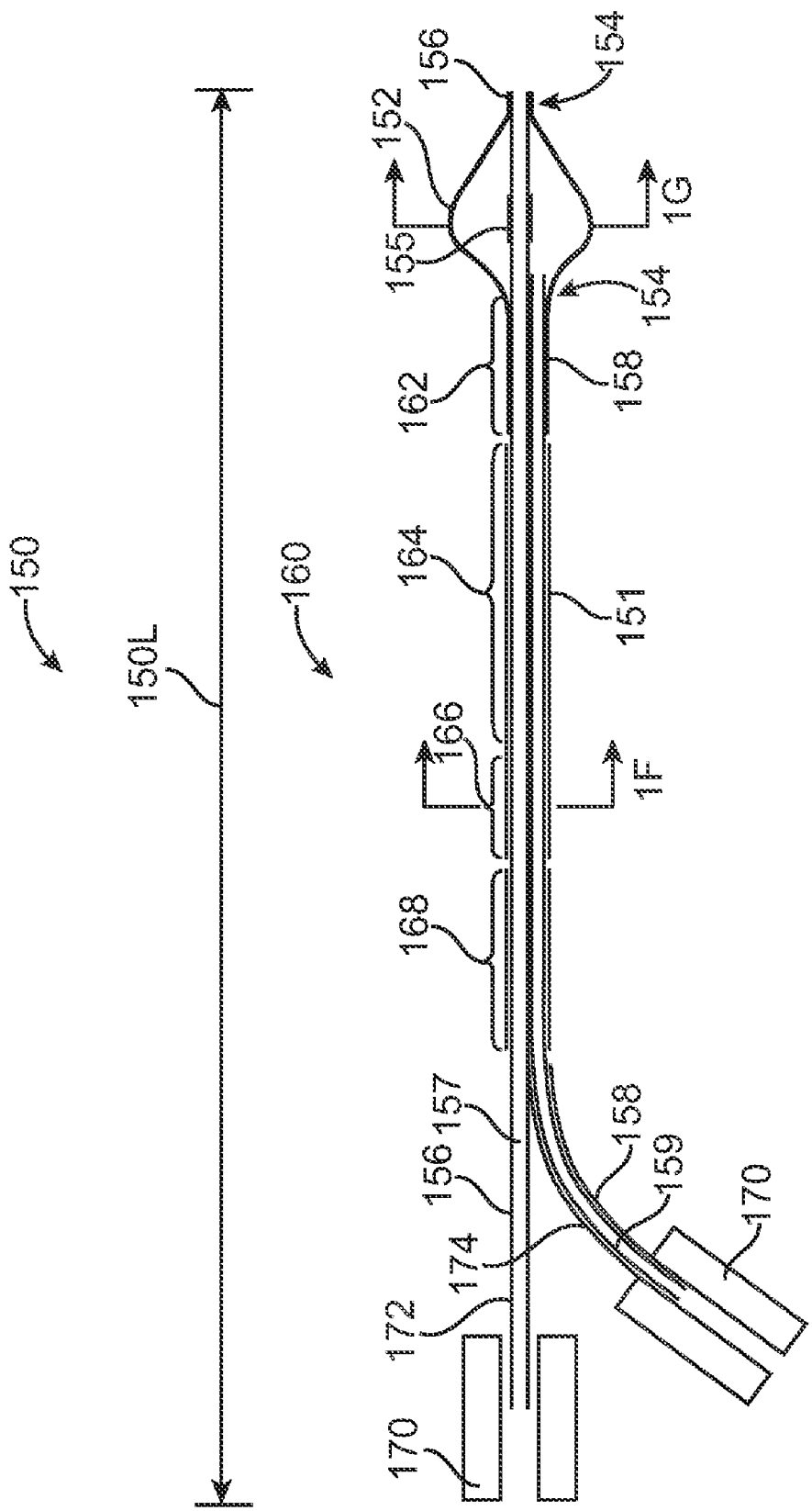
FIGS. 1E to 1G show components of the catheter as in FIGS. 1B to 1D, according to embodiments of the present invention.
Figure 1F:
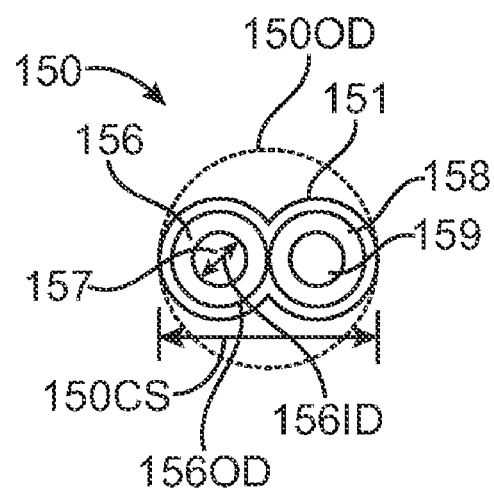
Figure 1G:
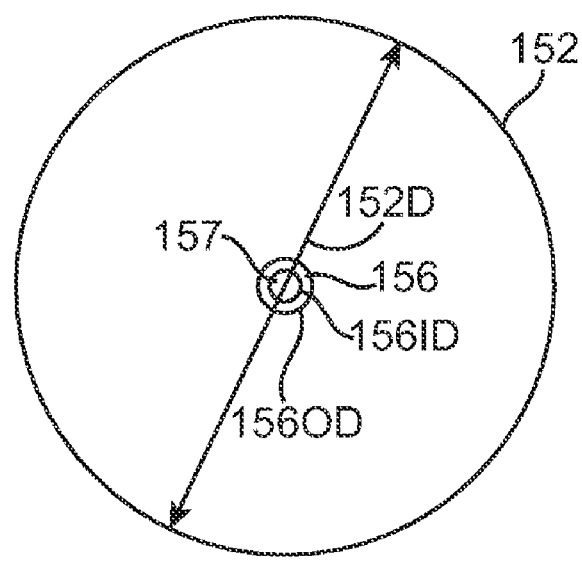

Referring now to FIGS. 1E to 1G, components of catheter 150 as in FIGS. 1B to 1D are shown, according to embodiments of the present invention. Catheter 150 may comprise a micro-catheter with a body 151 having a flexible shaft. In many embodiments, catheter body 151 comprises a polymeric tube having a central passageway, which receives the inflation tube and the injection tube. Catheter 150 comprises a length 150L. Length 150L of the catheter may comprise a range of lengths, for example a range from about 30 to 62 cm. In this system, the catheter may comprise a polymer balloon located near the distal tip. An anchor, for example balloon 152, may comprise many anchors, for example as described in U.S. Pat. App. Pub. No. 2005/0234425, the full disclosure of which has been previously incorporated herein by reference. An injection tube 156 may extend from a proximal end of catheter 150 to a distal end of the catheter. Injection tube 156 may comprise an injection lumen 157. An inflation tube 158 may extend from the proximal end of the catheter to a distal portion of the catheter near balloon 152. Inflation tube 158 may comprise an inflation lumen 159. Injection tube 156 and inflation tube 158 may comprise many materials, and in some embodiments may comprise stainless steel tubes that are contained inside a polymer shaft of catheter 150. The inflation lumen can be used for inflating and deflating the balloon, and the injection lumen can be used for injection of substances such as radiopaque contrast agents, local anesthetics, antibiotics and/or preservative-free saline solution. Bonds 154 may attach balloon 152 to injection tube 156. Bonds 154 may comprise many types of bonds, for example UV adhesive bonds and/or heat bonds. Bonds 154 may attach balloon 152 near a distal end of injection tube 156 and near a distal end of inflation tube 158. Once catheter 150 has been properly positioned, balloon 152 can be inflated with a radiopaque contrast medium, and balloon 152 may assist in maintaining proper catheter placement during the functional testing portion of the procedure. Following this procedure, the balloon may be deflated to facilitate removal of catheter 150.

In many embodiments, a radiopaque marker 155 may be disposed on a catheter 150, for example located centrally within balloon 152. Radiographic marker 155 may facilitate positioning of balloon 152 in disc D. Radiopaque marker 155 may comprise a many known radiopaque materials.

Tuohy Borst adapters 170 may be connect to proximal ends of injection tube 156 and inflation tube 158, for example after catheter 150 has been placed.

Injection tube 156 may comprise a color coded sheath 172, and inflation tube 158 may comprise a color coded sheath 174 to distinguish the injection lumen from the inflation lumen. For example color coded sheath 172 may comprise green to indicate injection tube 156 and injection lumen 157, and color coded sheath 174 may comprise red to indicate inflation tube 158 and inflation lumen 159. Such colors are merely illustrative and many combinations can be used, for example white can be used instead of green and blue can be used instead of red. In some embodiments, the injection lumen and/or tube can be distinguished from the inflation lumen and or tube by the length of the tubes. For example, the inflation tube and/or lumen may be shorter with a proximal end that is distal to the proximal end of the inflation lumen, such that the balloon Tuohy Borst Adapter is distal to the injection Tuohy Borst adapter.

In many embodiments, catheter 150 comprises indicia over at least a proximal portion of the length of the catheter to indicate the position of the distal end of the catheter in relation to a structure on the placement instrument, for example the distal end of the inner needle. The indicia may comprise a scale formed, printed or etched on a surface of the catheter. In some embodiments, the indicia may comprise color coding, for example a color change that corresponds to a position of the catheter in relation to the inner needle. Many indicia and coding schemes may be used to indicate the location of the catheter with respect a placement instrument. In many embodiments, catheter 150 may comprise color coded indicia to mark the location of catheter 150 as it passes through the inner needle. The indicia on the catheter may comprise reticules, scales gauges and the like, in addition to or in combination with color encoding, and many known methods of marking catheters may be used to encode the position of the catheter in relation to the inner needle. In some embodiments, catheter 150 may comprise indicia with color encoding 160 to indicate the depth of the catheter in the patient. The indicia comprising color encoding 160 may comprise a clear section 162 that may include balloon 152. Encoding 160 may comprise a black section 160 to indicate that a distal tip of catheter 150 has not yet reached a distal opening of the inner needle that exits to the disc. Encoding 160 may comprise a green section 166. A distal boundary of green section 166 with black section 164 may indicate that the distal tip of catheter 150 is near the opening to the inner needle. Encoding 160 may comprise a black section 168. A transition from green section 166 to black section 168 may indicate that the balloon has exited the catheter port and that the distal tip of the catheter extends from the opening into the disc by a pre-determined distance. Additional indicia may be included that correspond to locations of additional structures of the catheter in relation to the inner needle.

In some embodiments, the catheter can be encoded to accommodate two inner needle lengths, which can be particularly helpful when the two inner needles are provided, for example provided in a kit, in a system or separately. For example, the catheter may comprise a yellow, green, yellow color scheme, and the kit may comprise outer needles of 9 cm and 13 cm. When the tip of the catheter is at the tip of the shorter of the two inner needles, the color transition of the catheter at the needle hub goes from yellow to green. When the tip of the catheter is at the tip of the longer of the two inner needles, the color transition of the catheter at the needle hub goes from green to yellow.

Color coding can be performed in many ways. For example, the color coding could comprise printing a color with an ink, using a colored heat shrink, and/or laminating on a material to the tube. In some embodiments, color coding may comprise laser marking or laser etching. In addition to and/or in combination with color coding of the proximal tubes, the Tuohy Borst adapters may be color coded to indicate their purpose. In some embodiments, the inflation tube may be marked with a color that matches the color of a Tuohy Borst adaptor, or other adapter, that is marked "inflation". In some embodiments, the wing nuts may be color coded to correspond with the adaptors. The injection tube may be marked with a different color that matches the color of a Tuohy Borst adaptor that is marked "injection".

FIG. 1F shows a cross sectional view of catheter 150 near a middle section of the catheter, as in FIG. 1E. Catheter 150 comprises catheter body 151. Injection tube 156 comprises injection lumen 157. Injection tube 156 comprises an outer cross sectional size, for example outside diameter 156OD, and an inner cross sectional size, for example an inner diameter 156ID. Inner diameter 156ID corresponds to a cross sectional size of inflation lumen 157. Inflation tube 158 comprises inflation lumen 159. Inflation tube 158 comprises an outer cross sectional size, for example an outer diameter 158OD, and an inner cross sectional size, for example an inner diameter 158ID. Inner diameter 158ID corresponds to a cross sectional size of inflation lumen 157. Catheter 150 comprises an outer cross sectional size 150CS that corresponds to an outer diameter 150OD. In many embodiments, outer cross-sectional size 150CS and outer diameter 150OD may be no greater than 1.5 mm. In many embodiments, the outer cross sectional size and/or outer diameter can be sized to fit through a 0.9 mm, or 20 gauge, needle with an inner lumen of about 0.023 inches, or about 0.5 mm, such that the catheter is capable of passing through the lumen of the inner needle. In specific embodiments, the outer cross sectional size and/or outer diameter may comprise a size of about 0.020 inches, or about 0.5 mm. In many embodiments, outer cross sectional size 150OS may be defined by catheter body 151.

The needles sizes described herein are merely illustrative according to some embodiments, and one will recognize that many sizes of needles can be used. In many embodiments, dimensions listed herein correspond to known ISO standards and the normal ranges of needle dimensions in accordance with these known ISO standards. For example, a metric size needle of 0.7 corresponds to a 22 gauge needle with a range of outside diameters from about 0.698 mm to about 0.730 mm and inside diameters of about 0.390 mm to about 0.522 mm. A metric size of 0.9 corresponds to a 20 gauge needle with a range of outside diameters from about 0.860 mm to about 0.920 mm and inside diameters of about 0.560 mm to about 0.687 mm. A metric size of 1.2 corresponds to a 18 gauge needle with a range of outside diameters from about 1.200 mm to about 1.300 mm and inside diameters of about 0.790 mm to about 1.041 mm.

FIG. 1G shows a cross sectional view of catheter 150 near a distal portion of the catheter with balloon 152 in an expanded configuration. Injection tube 156 comprises an outer diameter 156OD and inner diameter 156ID. Balloon 152 comprises a cross sectional size, for example a diameter 152D. In a specific embodiment, diameter 152D may comprise a size of about 0.010 inches in the inflated configuration so as to anchor the catheter in the disc interior. In an unexpanded and/or non-inflated configuration balloon 152 may comprise a cross sectional size to fit through the inner needle.

In many embodiments, the catheter may comprise high axial force transmitting material, and the catheter may be reinforced with a reinforcement component such as wire, thread, and/or filament to increase axial strength. The reinforcement component may comprise a metal, for example at least one of stainless steel, tungsten, Elgiloy, platinum molybdenum, iridium or nitinol and/or other metals. In some embodiments, the reinforcement component may comprise alloys, for example at least one of platinum-iridium, platinum-tungsten, molybdenum-rhenium, or tungsten-rhenium and/or other alloys. In some embodiments, the reinforcement component may comprise polymers such as PEEK, Kevlar or Dacron, and/or other polymers. In some embodiments the reinforcement component may comprise braids and/or twisted strands of metals, metal alloys and/or polymers. The reinforcement component may be disposed on at least one of the catheter body, the injection tube or the inflation tube. The reinforcement component may be disposed over the catheter body and/or tubes, and in some embodiments can be embedded in such structures.

Embodiments of the present invention may use functional evaluation of the disc. Functional evaluation may comprise pain provocation and careful assessment of the patient's response to pain. A substance can be injected into the nucleus pulposus that may reduce pain perceived by the patient. For example, if the patient reports a decrease in pain after injection of the substance into the disc, the disc may contribute to pain previously perceived by the patient and the identified defective disc may be corrected surgically.

Several substances may be injected into the nucleus pulposus to perform the functional evaluation. In some embodiments, at least one of the following substances can be introduced: an anesthetic; an analgesic; an antibiotic; a hydrating agent such as hypotonic saline, isotonic saline or hypertonic saline; a supportive agent such as a hydrogel, ethylene-vinyl alcohol copolymer, Dimethyl Sulfoxide or Tantalum; a prolotherapy agent such as sodium morrhuate, cod oil, phenol, minerals or ethyl alcohol; and other agents such as collagen, stem cells, Osteogenic Protein-1, ethanol, alcohol, steroids, radio-opaque contrast agents, ultrasound contrast agent, Bone Morphogenetic Protein (BMP), BMP-2, BMP-4, BMP-6, BMP-7, BMP-12, Serotonin 5-HT2A receptor inhibitors, LMP-1, TIMP-1, TGF-1, TGF-2, Rofecoxib, Ketorolac, Glucosamine, Chondroitin Sulfate, Dextrose, DMSO, non-steroidal antiinflammatory drugs, ibuprofen, naprosyn, Bextra, Vioxx, Celebrex, indomethacin, botulinum toxin, capsaicin, vanilloid agonists, vanilloid antagonists, VR1, VRL-1, steroids, methylprednisolone or chymopapain; cells, cell fragments, tissue, tissue gragments; genetic material, such as DNA, cDNA, RNA, mRNA, rRNA, siRNA, tRNA, plasmids, lentivirus, adenovirus, adeno-associated virus, or derivatives or fragments or synthetic mimics thereof, cytokines, growth factors, differentiation factors, hormones, ligands, receptors; intracellular regulatory molecules, or transcription factors, or their agonists, antagonists, activators, or inhibitors, or derivatives or fragments of synthetic mimics thereof, matrix molecules such as fibrin, collagen, proteoglycans, glycosaminoglycans, polysaccharides, elastin, or derivatives or fragments or synthetic mimics thereof; matrix-regulating molecules such as crosslinking agents, link protein, metalloproteinases, or enzymes, or their activators or inhibitors, or derivatives or fragments or synthetic mimics thereof, drugs such as statins, purmorphamine, anti-inflammatory drugs; neurotransmitting agents or neurotoxic agents or their inhibitors; MRI contrast agents; bone fillers, bone graft materials, and bone graft substitutes such as bone autograft, bone allograft, anorganic bone matrix, demineralized bone matrix, calcium phosphate, tricalcium phosphate, calcium sulfate, hydroxyapatite, bioglass, polymers, or combinations thereof; additional biologic-based, biologic derived, or biologic-mimicking substances; and substances used for controlled release of any of the above substances, such as polymers, liposomes, self-assembling monolayers, tie-layer molecules, scaffolds, or gels, for example hydrogels.

In some embodiments, the substance can be injected to alter the pH of the nucleus. In specific embodiments directed to diagnosis, raising the pH can make the nucleus and surrounding tissues more basic so as to lower the threshold of triggering nociceptive receptors. Such pH lowering substances can also be injected into the patient in therapeutic embodiments.

Figure 2A:
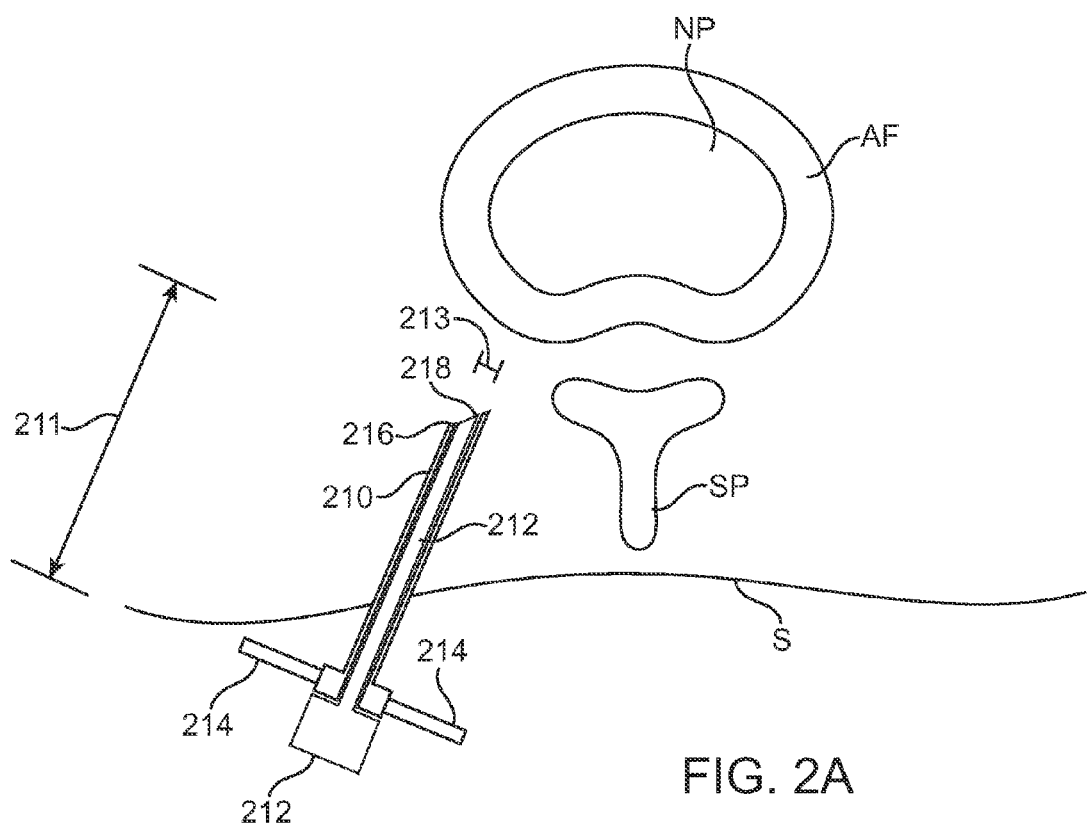
FIG. 2A shows an outer needle and a stylet, according to embodiments of the present invention.

Referring now FIG. 2A, an outer needle 210 and stylet 212 are shown, according to embodiments of the present invention. Outer needle 210 can be used to access the disc, particularly, in the area adjacent to the intradiscal space to facilitate sequential placement of the inner needle and catheter into the intradiscal space. Outer needle 210 may comprise many materials such as metal or plastic (e.g. retinol, cobalt chrome, PEEK, stainless steel). Outer needle 210 can comprise many sizes that access the tissue surrounding the disc, and outer needle 210 can be sized to advance the inner needle to the interior of the disc. Outer needle 210 may comprise many lengths, for example a 1.2 mm outside diameter (18 gauge) needle 9 cm in length and a 1.2 mm outside diameter needle 13 cm in length. In some embodiments, outer needle 210 may be provided in a kit that includes two outer needles, for example a 1.2 mm diameter needle 9 cm in length and an 1.2 mm diameter needle 13 cm in length.

Stylet 212 can be sized to fit within a lumen of outer needle 210 and may comprise a length that matches needle 210. Stylet 212 may comprise many of the materials of outer needle 210. Outer needle 210 may comprise a bevel cut distal tip 216, and a stylet tip 218 may comprise a bevel cut that matches bevel cut needle tip 216. In many embodiments, outer needle 210 comprises an insert to inhibit coring. The insert may comprise at least one of a removable stylet, a trocar or an obturator, or the like, that can be removed from outer needle 210 after the outer needle has been positioned, so as to inhibit coring when the outer needle is placed in the tissue. Outer needle 210 comprises a length 211. Length 211 may comprise a range of lengths from about 3 to 30 cm and in some embodiments a range of lengths from about 3 cm to 20 cm. Outer needle 210 comprises an inner size, for example an inner diameter 213. In many embodiments, inner diameter 213 may comprise a diameter no more than about 1.7 mm.

Figure 2B:
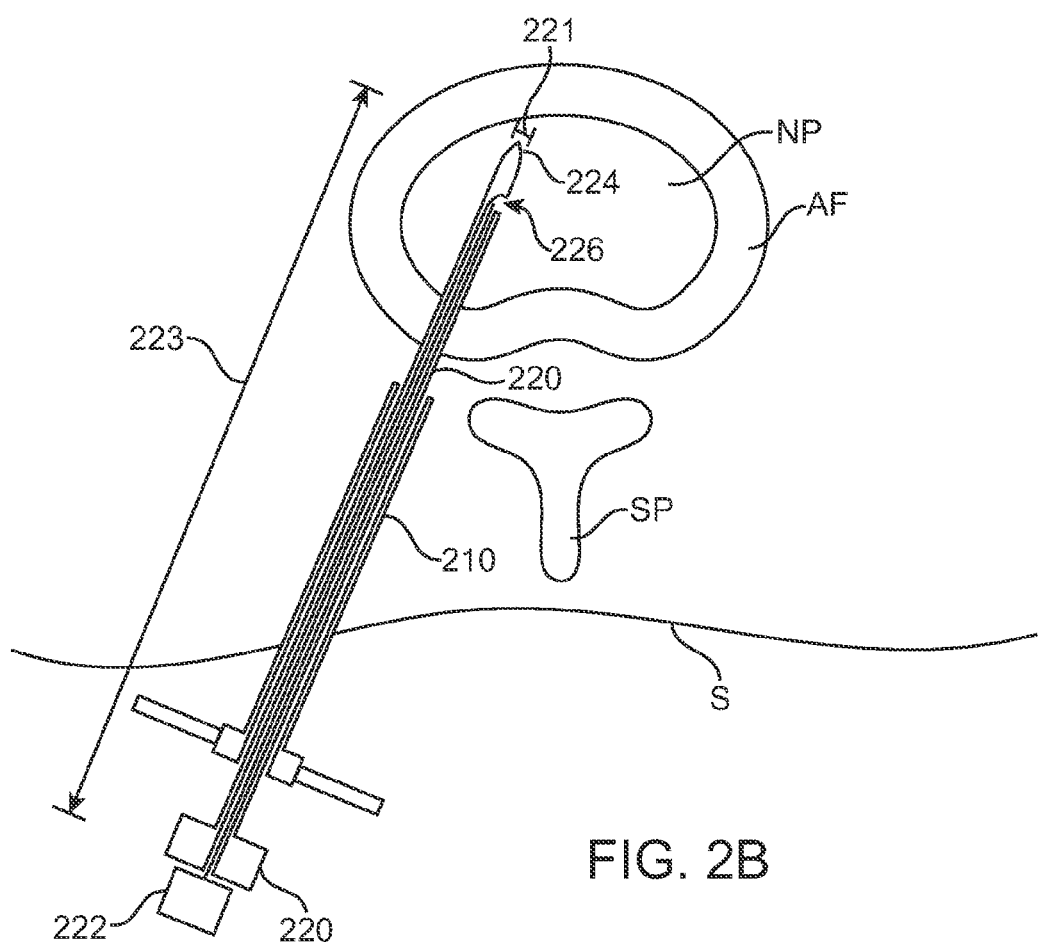
FIG. 2B shows an inner needle and inner needle stylet, according to embodiments of the present invention.

Referring now to FIG. 2B, an inner needle 220 and an inner needle stylet 222 are shown, according to embodiments of the present invention. Inner needle 220 can be used to access nucleus pulposus NP of the intervertebral disc and is capable of passing through annulus fibrosis AF. Inner needle 220 can be used to perform provocative discography and may facilitate placement of the catheter into the intradiscal space. Inner needle 220 may comprise an atraumatic needle that comprises a blunt tip 224 and a side port 226 that allows for delivery of the anchored catheter through side port 226. In many embodiments, the catheter can be delivered through side port 226 without a guide wire. Inner needle 220 may comprise many materials such as metal or plastic (e.g. retinol, cobalt chrome, PEEK or stainless steel). Inner needle stylet 222 may comprise many materials similar to inner needle 220. Inner needle 220 may comprise many size suitable sizes to access the nucleus of the intervertebral disc and deliver the anchored catheter to the intervertebral disc. Inner needle 220 comprises an outer cross sectional size, for example an outer diameter 221. In many embodiments, outer diameter 221 comprises a diameter no greater than about 1.5 mm. For example, outer diameter 221 of inner needle 220 may comprise a range of sizes from about 0.5 mm to about 0.9 mm. Inner needle 220 comprises a length 223. Length 223 of inner needle 220 may comprise a range of lengths from about 10 cm to about 30 cm. In some embodiments, inner needle 220 may be comprised within a kit that includes two inner needles comprising a 0.9 mm needle 18 cm in length and a 0.9 mm needle 10 cm in length. Both needles may comprise atraumatic tips.

Inner needle 220 may comprise many types of needle tips that are adapted to penetrate tissue. In many embodiments, needle 220 may comprise an atraumatic needle, for example a Sprotte needle commercially available from Pajunk Medical Systems of Tucker, Ga., and distributed by Havel's of Cincinnati Ohio, a Whittacre needle known in the art to perform spinal blocks, and other atraumatic needles, for example as described in U.S. Pat. No. 5,573,519, entitled "Atraumatic needle for lumbar puncture", in the name of Zohmann, the full disclosure of which is incorporated herein by reference. In some embodiments, an atraumatic needle may comprise pencil-point needle with a blunt tip and a sharp point. In many embodiments, the atraumatic needle comprises a blunt needle tip that separates the dura fibers, creating a small hole in the dura that closes. In some embodiments, the atraumatic needle may comprise a side port that minimizes tissue tearing along edges of the port.

Figure 2C:
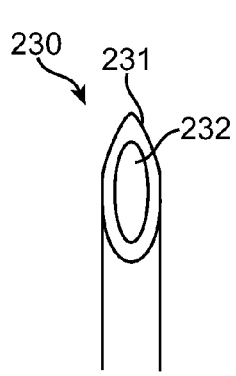
FIG. 2C shows an inner needle comprising a Quincke type needle, according to embodiments of the present invention.

Referring now to FIG. 2C, detail of an inner needle comprising a Quincke type needle 230 is shown, according to embodiments of the present invention. Quincke type needle 230 may comprise a sharp beveled end and an oval port 232. Sharp beveled end 231 can cut through tissue and may be desirable in some embodiments, for example tough tissue that an atraumatic with a non-cutting tip may have difficulty penetrating.

Figure 2D:
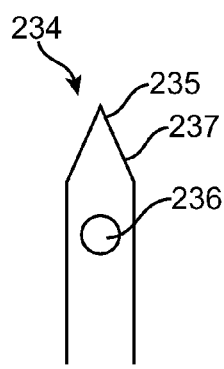
FIG. 2D shows an inner needle comprising a Whitacre type needle, according to embodiments of the present invention.

Referring now to FIG. 2D, an inner needle comprising a Whitacre type needle 234 is shown, according to embodiments of the present invention. Whitacre type needle 234 may comprise a blunt tip 237 with a sharp point 235, such that the needle may comprise an atraumatic needle. Whitacre type needle 234 may comprise a side port 236. Side port 236 may comprise many shapes including circular, oval, rectangular and combinations thereof, such that side port 236 permits the catheter to exit the needle through side port 236.

Figure 2E:
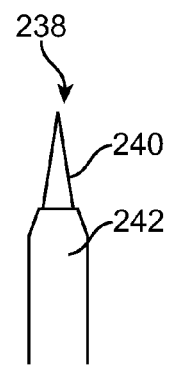
FIG. 2E shows an inner needle comprising a Levy type needle, according to embodiments of the present invention.

Referring now to FIG. 2E, an inner needle comprising a Levy type needle 238 is shown, according to embodiments of the present invention. Levy type needle 238 may comprise an annular needle 242 and an inner through needle 240. Inner through needle 240 may be removed after Levy type needle 238 has been positioned, such that the catheter can be passed though annular needle 242.

Figure 2F:
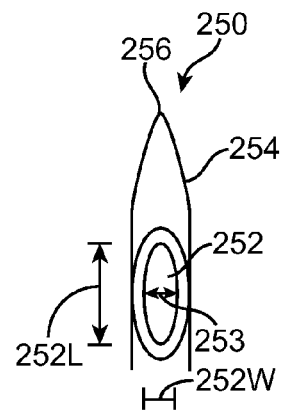
FIG. 2F shows an inner needle comprising a Sprotte type needle, according to embodiments of the present invention.

Referring now to FIG. 2F, an inner needle comprising a Sprotte type needle 250, for example a special Sprotte needle, is shown, according to embodiments of the present invention. Sprotte type needle 250 may comprise a side port 252. Side port 252 may comprise an elongate shape. For example, side port 252 can be shaped to permit the catheter to exit through the side of the inner needle with many elongate shapes including oval, rectangular and elliptical shapes. Side port 252 can comprise a length 252L and a width 252W. In many embodiments, an inner size of the inner needle, for example an inner diameter 253, may be at least 0.38 mm. Sprotte type needle 250 may comprise a blunt needle tip 254 with a sharp point 156. Blunt tip 254 may comprise many blunt shapes, for example a shape in the form of an ogive. Sprotte type needle 250 may cause less tissue damage than some other needle types. For example, the Sprotte needle may not cause nerve damage if the needle hits nerves intraoperatively. Side port 252 may comprise all metal edges that are smoothed, for example hand rounded, such that damage to a balloon passing through the port is unlikely. In some embodiments, the Sprotte needle may cause sufficiently less tissue damage than other needle types such that a larger diameter Sprotte needle may be used to place the catheter, thereby facilitating passage of the catheter through the needle.

Figure 2G:
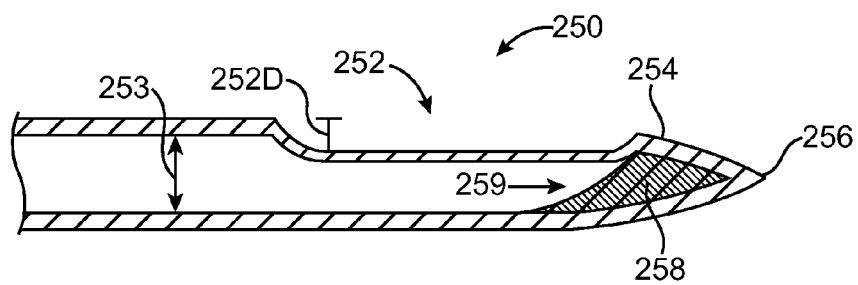
FIG. 2G shows a cross sectional view of a Sprotte type needle as in FIG. 2F, according to embodiments of the present invention.

Referring now FIG. 2G, a cross sectional view of Sprotte type needle 250 as in FIG. 2F is shown, according to embodiments of the present invention. The inner needle comprises an inner lumen with a size that corresponds to inner diameter 253 of the inner needle. Side port 252 may comprise a depth 252D cut into the inner needle. Side port 252 is positioned near a ramp 259. Ramp 259 may guide the catheter tip toward side port 252. Ramp 259 may be formed in many ways, for example with a material 258. Material 258 may comprise many materials, for example materials similar to the inner needle and stylet. In some embodiments material 258 may comprise a rigid filler material, for example epoxy. Side port 252 can be adapted to slide along the catheter while the side port is retracted proximally through the annulus in many ways including at least one of width 252W, length 252L or cut depth 252D.

Figure 2H:
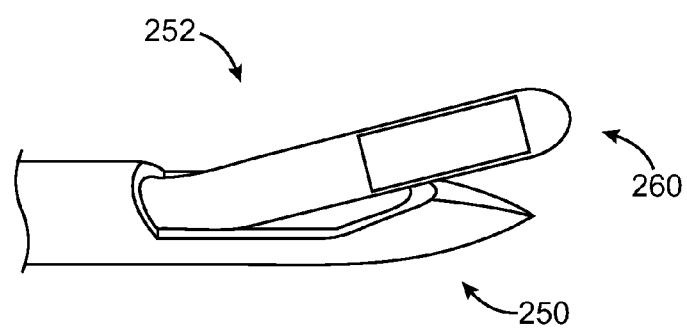
FIG. 2H shows a catheter exiting a side port of a Sprotte type needle as in FIGS. 2F and 2G, according to embodiments of the present invention.

Referring now to FIG. 2H, a catheter 260 is shown exiting side port 252 of Sprotte type needle 250 as in FIGS. 2F and 2G, according to embodiments of the present invention. Catheter 260 may comprise many of the catheter components described above. For example, catheter 260 may comprise a FAD catheter with an expandable balloon that can fit through side port 252. In many embodiments, catheter 260 comprises a flexible distal tip that is capable of bending so as to pass through side port 252 upon deflection by ramp 259.

Figure 2I:
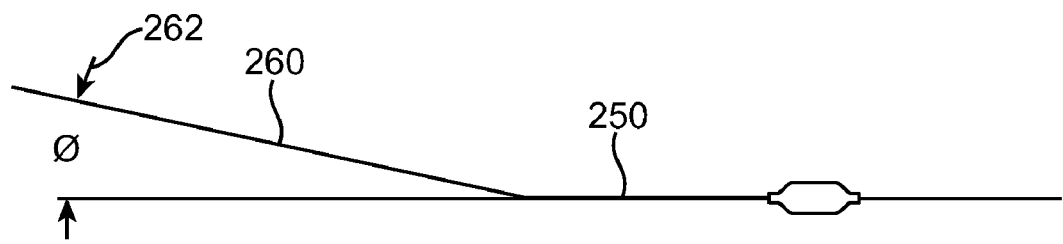
FIG. 2I, shows a deflection angle of the catheter through a needle as in FIGS. 2F to 2H, according to embodiments of the present invention.

Referring now to FIG. 2I, a deflection angle 262 of catheter 260 through a needle port as in FIGS. 2F, 2G and 2H is shown, according to embodiments of the present invention. Deflection angle 262 may comprise an angle between the inner needle with the side port, for example Sprotte needle 250, and the catheter that extends from the side port toward the distal end of the catheter. In some embodiments, angle 262 comprises a range from about 5 degrees to about 35 degrees and may comprise a range from about 10 degrees to about 15 degrees. Angle 262 may comprise a predetermined angle determined by at least one of length 252L of the side port, width 252W of the side port and an angle of inclination of ramp 259.

Figure 2J:
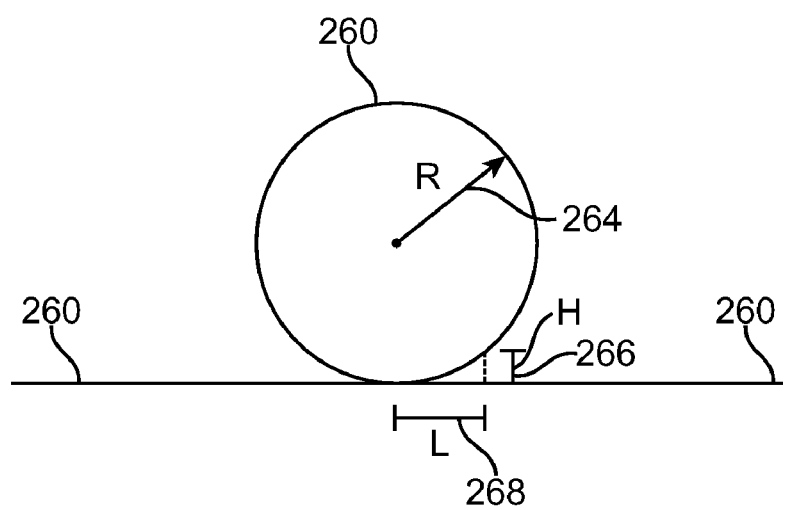
FIG. 2J shows a bend radius of the catheter as in FIGS. 2F to 2I, according to embodiments of the present invention.

Referring now to FIG. 2J, a bend radius 264 of catheter 260 is shown, according to embodiments of the present invention. Bend radius 264 comprises a known method of measuring the flexibility of a catheter. Bend radius 264 can be measured by forming a loop on the catheter and pulling on the catheter. Bend radius 264 may comprise a range from about 5 to 15 mm. In specific embodiments, bend radius 215 can be about 8 mm. In some embodiments, bend radius 264 approximates a slope comprising a length 268 and a height 266 that corresponds to deflection angle 262. In specific embodiments, the bend radius corresponds to the length, width and cut depth of the side opening in the catheter.

Figure 3A:
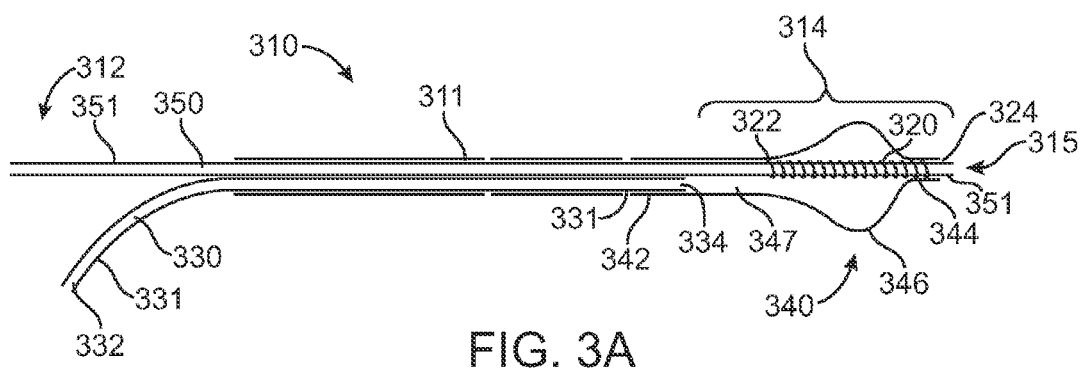
FIGS. 3A and 3B show a catheter that comprises a radiopaque coil and an inflation lumen, in which the inflation lumen terminates proximal to a proximal end of an expandable balloon anchor, according to embodiments of the present invention.
Figure 3B:
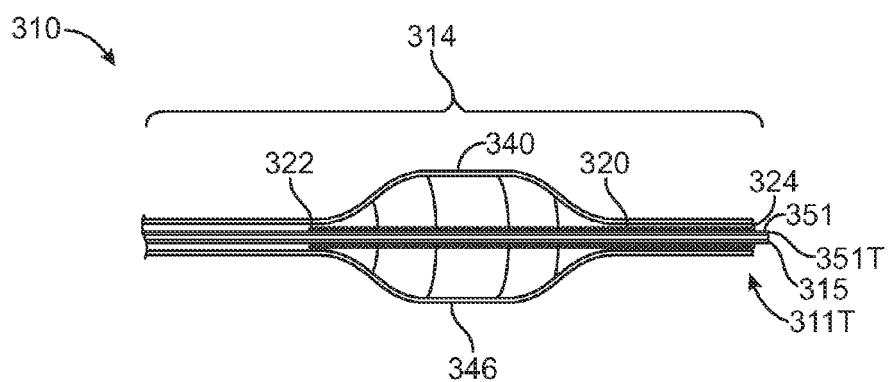

Referring now to FIGS. 3A and 3B, a catheter 310 is shown that comprises a radiopaque coil 320, an inflation lumen 330 and an injection lumen 350. Catheter 310 may comprise a catheter body 311 that comprises a proximal portion 312 and a very flexible distal portion 314. Flexible distal portion 314 may terminate distally at distal end 315 of the catheter. Inflation lumen 330 can comprise a proximal end 332 and a distal end 334. A tube 331 can define inflation lumen 330. An injection tube 351 can define injection lumen 350. In many embodiments, flexible distal portion 314 may be more flexible than the portion of the catheter that includes inflation tube 331. Catheter body 311 may comprise a polymeric tube having a central passage which receives the inflation tube and the injection tube. Radiopaque coil 320 may comprise a proximal end 322 and a distal end 324, such that coil 320 extends over flexible distal portion 314.

Radiopaque coil 320 can facilitate placement of the catheter with x-ray and/or fluoroscopy and may provide safety advantages. In many embodiments, the coil can easily flex with distal end portion 314. In specific embodiments, the coil may extend from a distal tip of the injection tube 351T to proximal portion 312 of the catheter so as to provide safety advantages. For example, if the distal shaft of the catheter comprising flexible distal portion 314 were to break, the coil may permit the broken catheter to be removed as one piece as the coil may retain the broken distal portion, such that the broken distal portion may be removed with the intact proximal portion of the catheter. In some embodiments, the flexible coil may extend from distal tip 351T to a proximal portion of the catheter located near the distal end of inflation tube 331, so as to provide similar retention of the distal portion.

Catheter 310 may comprise an inflatable balloon anchor material 340. Balloon anchor material 340 may comprise a proximal portion 342, a distal portion 344 and an expandable anchor portion 346 therebetween. Proximal portion 342 of balloon anchor material 340 can be fixed to inflation tube 331 with many techniques and/or substances, for example adhesives and/or curing as described above. Distal portion 344 of balloon anchor material 340 can be connected to injection tube 351 with many techniques and or substances as described above. In many embodiments, the proximal and distal portions of the balloon material may be thicker such that these portions may not expand substantially during inflation of the balloon and may not anchor the catheter. In some embodiments, the expandable anchor portion of the balloon material may comprise folds and may be thinner than the proximal and distal portions such that the expandable anchor portion can expand substantially to anchor the catheter with the balloon.

In many embodiments, distal end 334 of inflation tube 331 and inflation lumen 330 may terminate proximal to expandable anchor portion 346 of balloon anchor material 340, such that distal portion 314 of catheter 310 can be flexible. For example, inflation tube 331 may terminate with distal end 334 a distance from distal end 315 of the catheter in a range from about 3.8 to 7.6 cm. Such a distance can be sufficient in many patients to position the balloon anchor centrally in the disc space, for example centrally in the nucleus pulposus, and have distal end 334 of the inflation tube and the inflation lumen positioned away from the annulus and nerve roots. In some embodiments, the distal end of the inflation tube may lie at least about 5.5 mm proximally of the distal tip of the catheter body. In many embodiments, injection tube 351 extends distally beyond the distal end of inflation tube 331 and terminates near a distal tip 311T of the catheter body. In specific embodiments, injection tube 351 extends distally beyond a distal end of the expandable portion of the anchoring balloon by a distance of at least about 2 mm.

In some embodiments, proximal portion 324 of balloon anchor 340 does not expand substantially and may comprise a lumen 347. Lumen 347 can provide fluid communication with expandable portion 346, inflation tube 331 and inflation lumen 330, such that fluid from inflation tube 331 can pass through lumen 347 to expandable portion 346 to inflate the expandable portion.

Figure 3C:
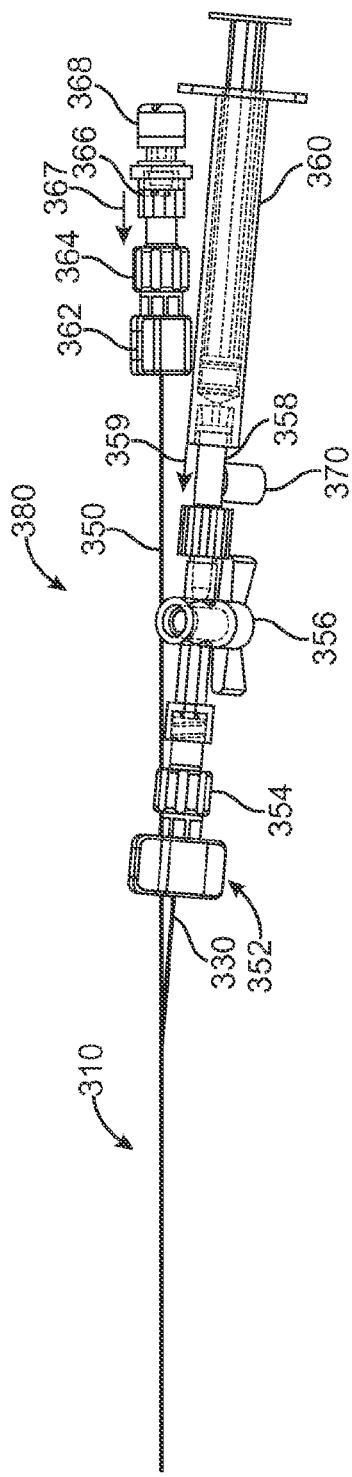
FIG. 3C shows inflation components and injection components connected to an inflation lumen and an injection lumen, respectively, according to embodiments of the present invention.

Referring now to the schematic illustration of FIG. 3C, inflation and injection components 380 are shown connected to an inflation lumen and an injection lumen, respectively, according to embodiments of the present invention. Catheter 310 may comprise inflation lumen 330 and injection lumen 350, as described above. A wing nut 352 can be connected to a Tuohy Borst connector 354. Wing nut 352 can facilitate attachment of at least some of components 380. Tuohy Borst connector 354 can connect to the inflation lumen and tube. A stopcock 356 can be connected to Tuohy Borst connector 354. Stopcock 356 comprises an isolation valve that can be used to shut off fluid flow to inflation lumen 330 and components 380 that are distal to stopcock 356. In some embodiments, a one way valve, for example a check valve 358, may be connected to stopcock 356. Check valve 358 may ensure that fluid flows one way in a proximal to distal direction, as shown by arrow 359. In some embodiments, components 380 may include a pressure relieve structure that comprises a pressure relief valve 370. Pressure relief valve 370 can be connected to stopcock 356 and check valve 358, such that fluid that exits check valve 358 can enter either stopcock 356 or pressure relief valve 370. A syringe 360 can be connected to check valve 358. In many embodiments, fluid flow from a proximal to a distal direction may comprise downstream flow, and fluid flow from a distal to proximal direction may comprise upstream fluid flow.

Syringe 360 can be connected to inflation lumen 330 such that syringe 360 can inflate the balloon anchor. In many embodiments, fluid that passes through check valve 358 enters stopcock 356 to inflate the balloon until the balloon reaches a desired predetermined pressure. When the inflation lumen and balloon reach the desired predetermined pressure, pressure relief valve 370 can open, such that fluid passes through pressure relief valve 370 to an exit port in a visible manner such that the clinician knows the desired predetermined pressure has been reached. In embodiments that include one-way check valve 358, the clinician may release syringe 360 and then close the valve stopcock 356. Some embodiments may not include check valve 358, and the clinician may close the valve of stopcock 356 while pressure is applied to syringe 360 to retain pressure and prevent reverse flow from the balloon back into the syringe. Once stopcock 356 is closed, the balloon may be subjected to additional pressure up to the burst pressure of the balloon.

Although the components are shown between syringe 360 and inflation lumen 330 in an illustrated order, many additional component combinations and/or component orders are possible. For example, the pressure relief valve can be installed distal to the stopcock, such that the balloon can vent through the pressure relief valve after the stopcock is closed. This may allow the balloon to release fluid through the pressure relief valve in response to the balloon being subjected to additional pressure after the stopcock has closed, for example when the patient moves. In some embodiments, the pressure relief valve may be located on the stopcock.

Components 380 may comprise several components that are connected to injection lumen 350. A Tuohy Borst connector 364 can be connected to injection lumen 350. A wing-nut 362 can be connected to Tuohy Borst connector 364. In some embodiments, a one-way valve, for example check valve 366, can be connected to the Tuohy Borst connector to provide one-way fluid flow in a proximal to distal downstream direction as indicated by arrow 367. The one-way valve can prevent upstream backflow of substances through the injection lumen. A connector 368 can be connected to a syringe to inject substances into the disc through injection lumen 350.

Figure 3D:
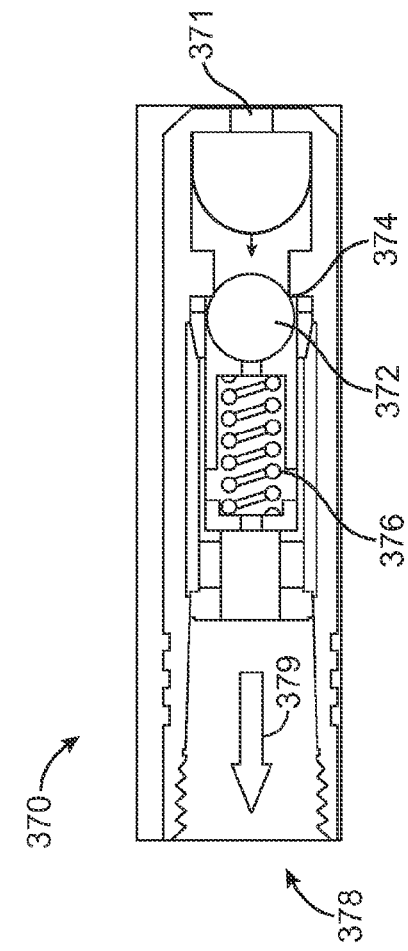
FIG. 3D shows components of a pressure relief valve, according to embodiments of the present invention.

Referring now to FIG. 3D, components of pressure relief valve 370, which comprises check valve, are shown according to embodiments of the present invention. Pressure relief valve 370 comprises an opening 371 in fluid communication with syringe 360 such that fluid from syringe 360 can pass into pressure relieve valve 370 under pressure. Pressure relive valve 370 comprises a ball 372 that contacts a seat 374 to form a seal. A spring 376 applies pressure to ball 372. Spring 276 can be selected such that ball 372 with separate from seat 374 at a selected and/or predetermined pressure, for example about 150 psi. In many embodiments, the selected and/or pre-determined pressure corresponds to the desired inflation pressure to the balloon. In specific embodiments, a balloon may have a rated pressure of 300 psi, and spring 376 selected such that pressure relief valve 370 releases fluid at about 150 psi. In some embodiments, the predetermined pressure may comprise a range from about 680 kPa to about 1620 kPa. Arrow 379 indicates the direction of fluid flow, for example liquid fluid flow, into an exit port 378 of the pressure relief valve. In many embodiments, fluid flows out exit port 378 such that the fluid is visible to the user and the user can determine that pressure relieve valve 370 has cracked open and inflation lumen 360 and the balloon have reached the selected and/or predetermined pressure.

Pressure relief valve 370 may comprise a check valve that can only pass fluid in one direction. Pressure valve 370 comprises many components that are similar to check valve 358 and check valve 366 that provide one-way fluid flow. In some embodiments, the check valves that are used to provide one way flow may comprise springs that allow the one-way check valves to crack open and pass fluid with relatively little pressure, for example 69 kPa (10 psi), as compared to pressure relief valve 370 that may pass fluid at 1030 kPa (150 psi).

Figure 3E:
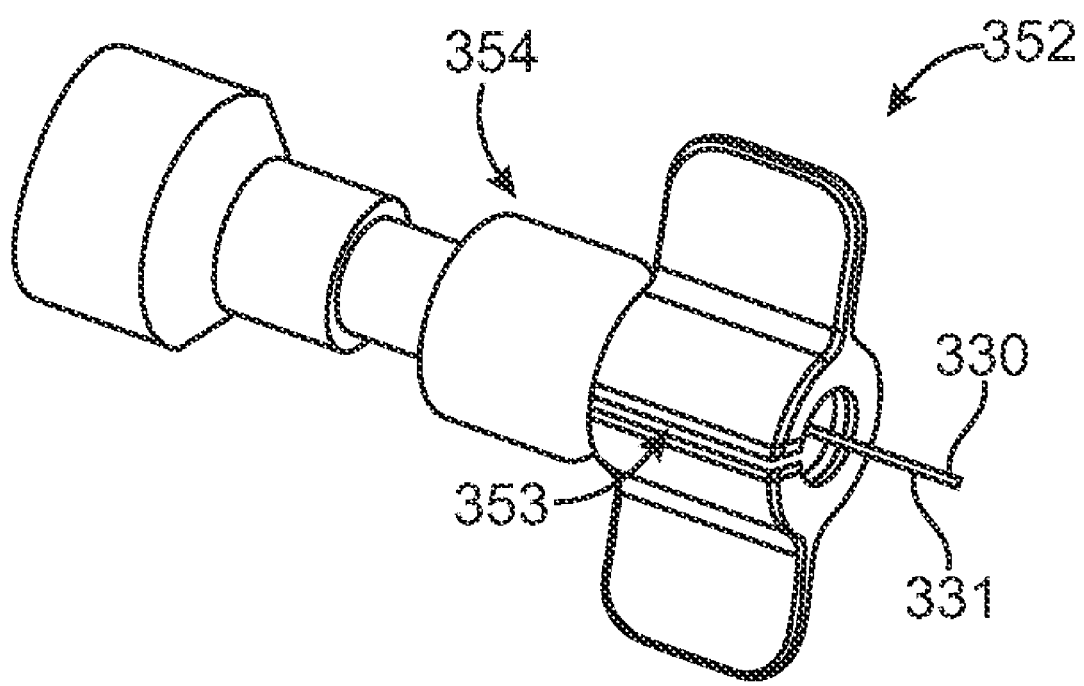
FIG. 3E shows a wing nut connected to a Tuohy Borst connector, according to embodiments of the present invention.

Referring now to FIG. 3E, wing nut 352 is shown connected to Tuohy Borst connector 354, according to embodiments of the present invention. Wing nut 352 can slide onto Tuohy Borst connector 354. Wing nut 353 comprises a slot opening 353 sized to pass lumen 330 of tube 331. Slot opening 353 permits removal of wing nut 352 over lumen 330 of tube 331, such that wing nut 352 can be removed from the catheter after tightening the Tuohy Borst connector while the Tuohy Borst connector is attached to the lumen. In many embodiments, wing nut 352 comprises a plastic wing nut made by injection molding, for example known ABS plastic injected into a mold using know injection molding techniques.

Figure 3F:
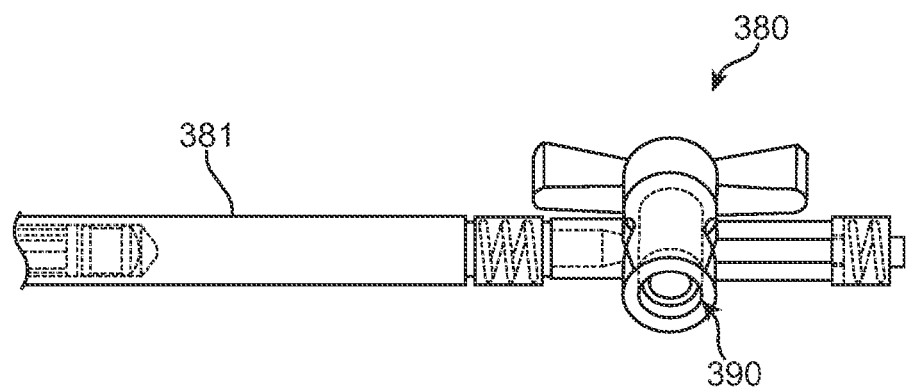
FIG. 3F shows a pressure relief valve integrated into a stopcock, according to embodiments of the present invention.

Referring now to FIG. 3F, a pressure relief valve 390 is shown integrated into a stopcock 380, according to embodiments of the present invention. Stopcock 380 can be connected to a syringe 381. Pressure relief valve 390 can be connected to the fluid path while the valve is open and isolated from the fluid path when the valve is closed. In some embodiments, the pressure relief valve and stopcock may comprise parts of the inflation syringe.

Figure 3G:
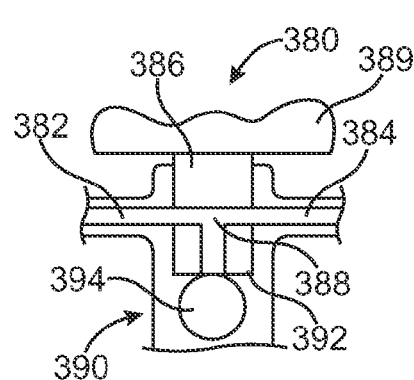
FIG. 3G shows a stopcock as in FIG. 3F in an open position, according to embodiments of the present invention.

Referring now to FIG. 3G, stopcock 380 as in FIG. 3F is shown in an open position, according to embodiments of the present invention. Stopcock 380 comprises a fluid inlet 382, a fluid outlet 384 and a cylindrical member 386 therebetween. Cylindrical member 386 comprises a channel 388. Channel 388 extends between inlet 382 and outlet 384 while the stopcock is open, such that inlet 382 is in fluid communication with outlet 384. Channel 388 extends to pressure relief valve 390. Pressure relief valve 390 may comprise a ball 394 and seat 392, similar to the ball and seat described above. Pressure from fluid in channel 388 can open the pressure relief valve. Pressure relief valve 390 may comprise a spring that allows valve 390 to open at a selected and/or predetermined pressure, as described above. A handle 389 can be rotated to close the stopcock and isolate pressure valve 390.

Figure 3H:
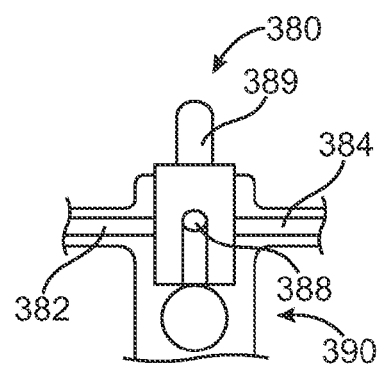
FIG. 3H shows a stopcock as in FIGS. 3F and 3G in a closed position, according to embodiments of the present invention.

Referring now to FIG. 3H, stopcock 380 is shown in a closed position according to embodiments of the present invention. Inlet 382 can be isolated from outlet 384 with rotation of handle 389, such that channel 388 does not connect inlet 382 with outlet 384. Handle 389 can also be rotated to open stopcock 380 such that channel 388 connects inlet 382, outlet 384 and valve 390.

The pressure relief valve may be located in many positions. In some embodiments, the pressure relief valve may be integrated into other areas of the components, such as in the body of the stopcock, or on a separate opening of the stopcock. The pressure relief valve may also be integrated into the syringe and/or as a separate device. In some embodiments, the pressure relief valve may comprise adjustable pressure relief valves, and the pressure relief valve may comprise visual and/or auditory signals to alert the user when the relief pressure has been reached. In some embodiments, the pressure relief valve may comprise a separate pressure relief valve, for example as available from Qosina of Edgewood, N.Y.

Figure 3I:
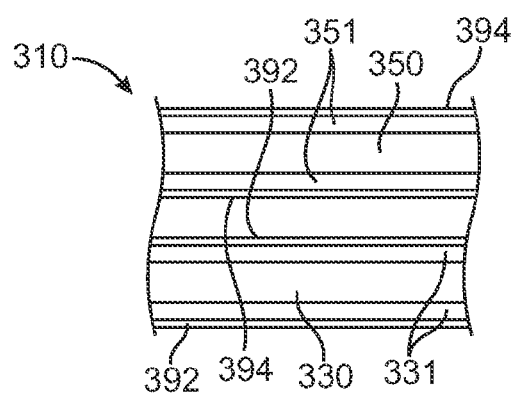
FIG. 3I shows a coating on the inflation tube and a coating on the injection tube, according to embodiments of the present invention.
Figure 4A:
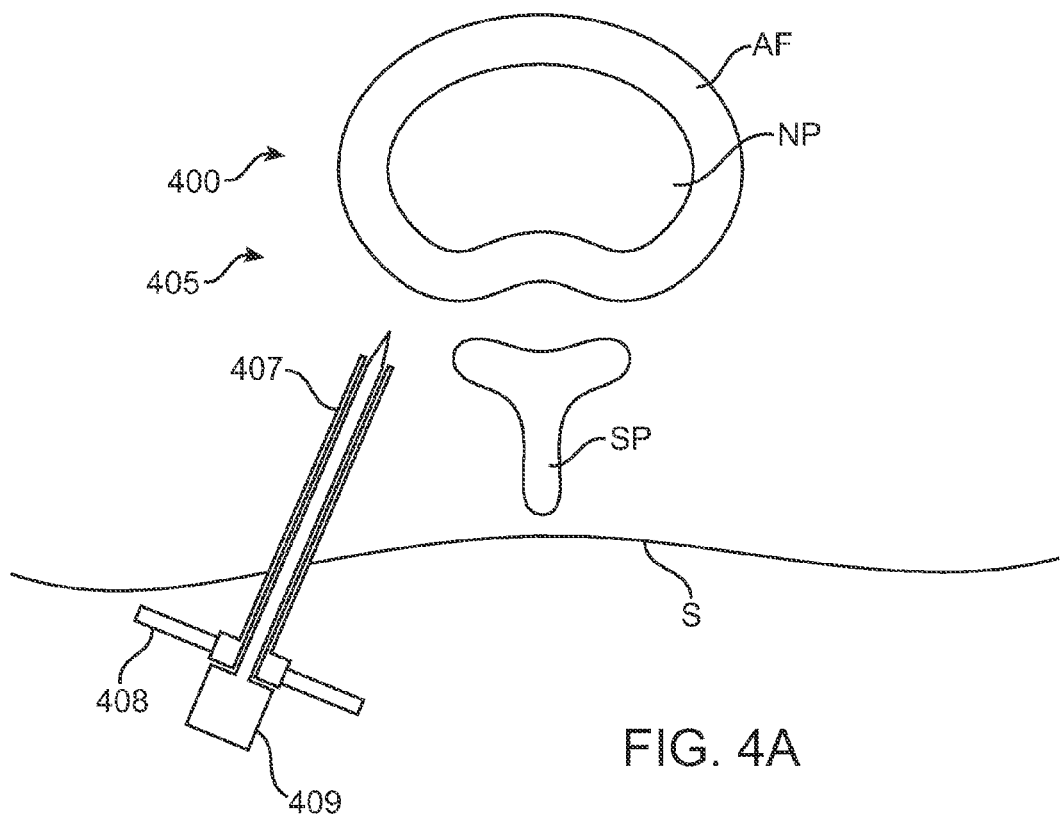
FIGS. 4A to 4J show a method of delivering a catheter with an atraumatic inner needle comprising a side port, according to embodiments of the present invention.
Figure 4B:
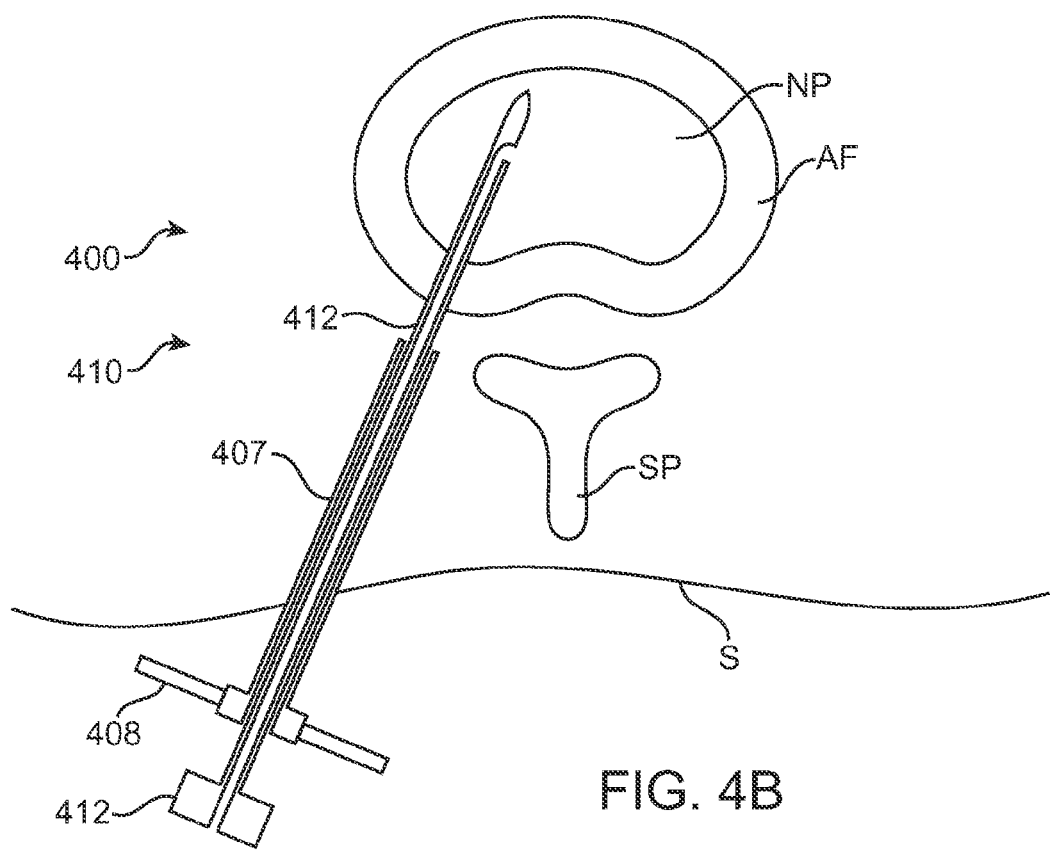
Figure 4C:
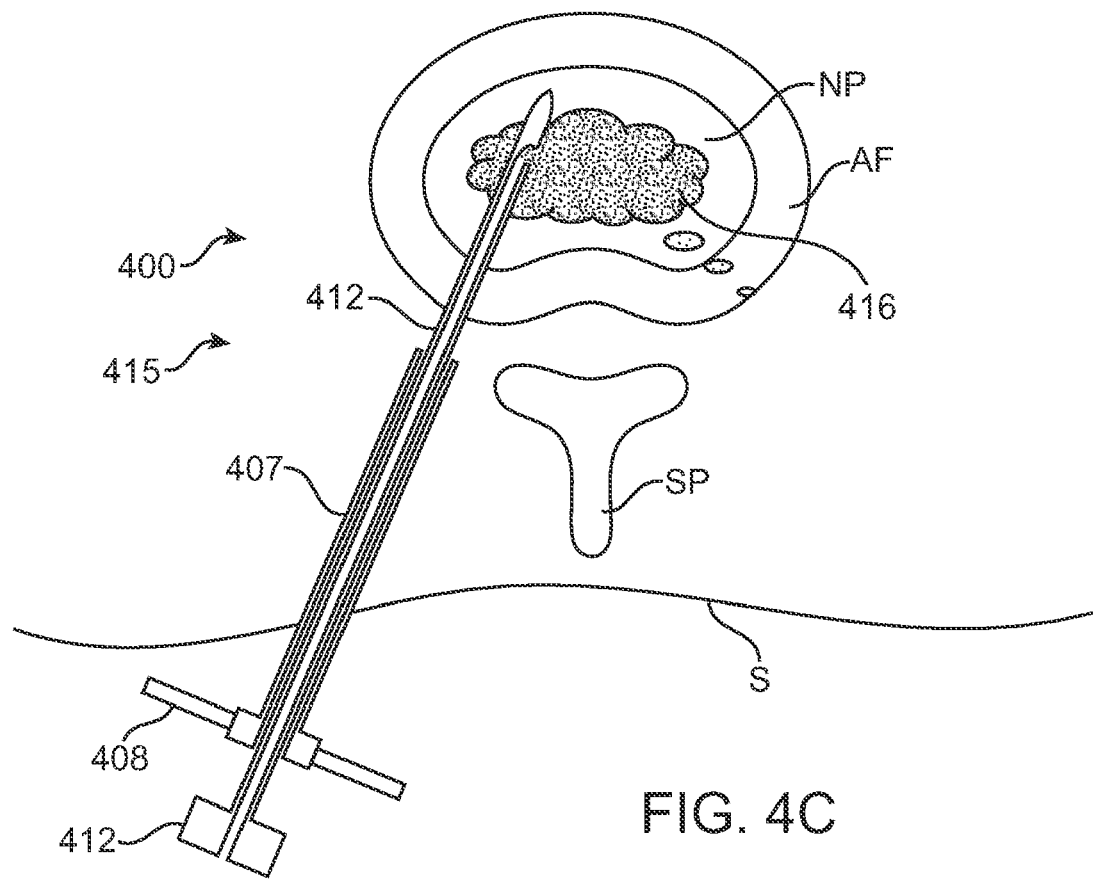
Figure 4D:
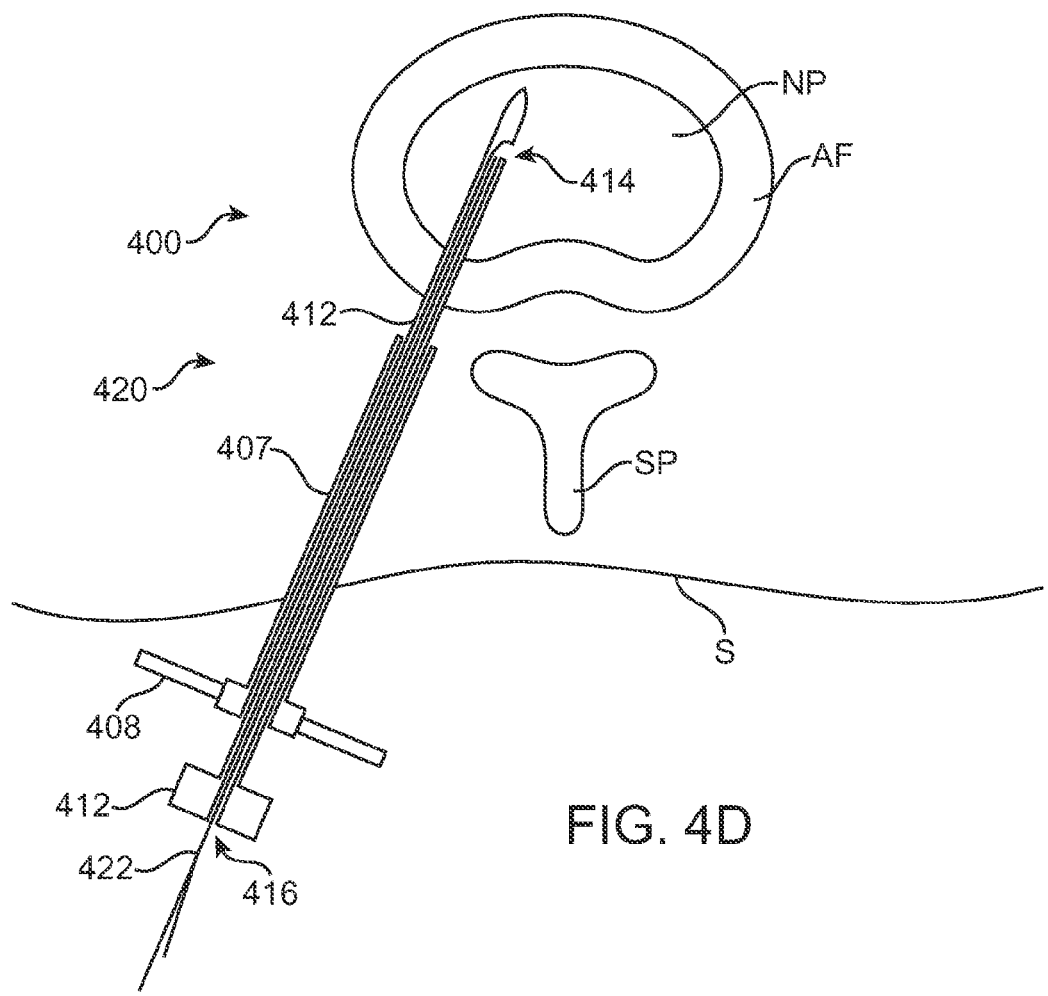
Figure 4E:
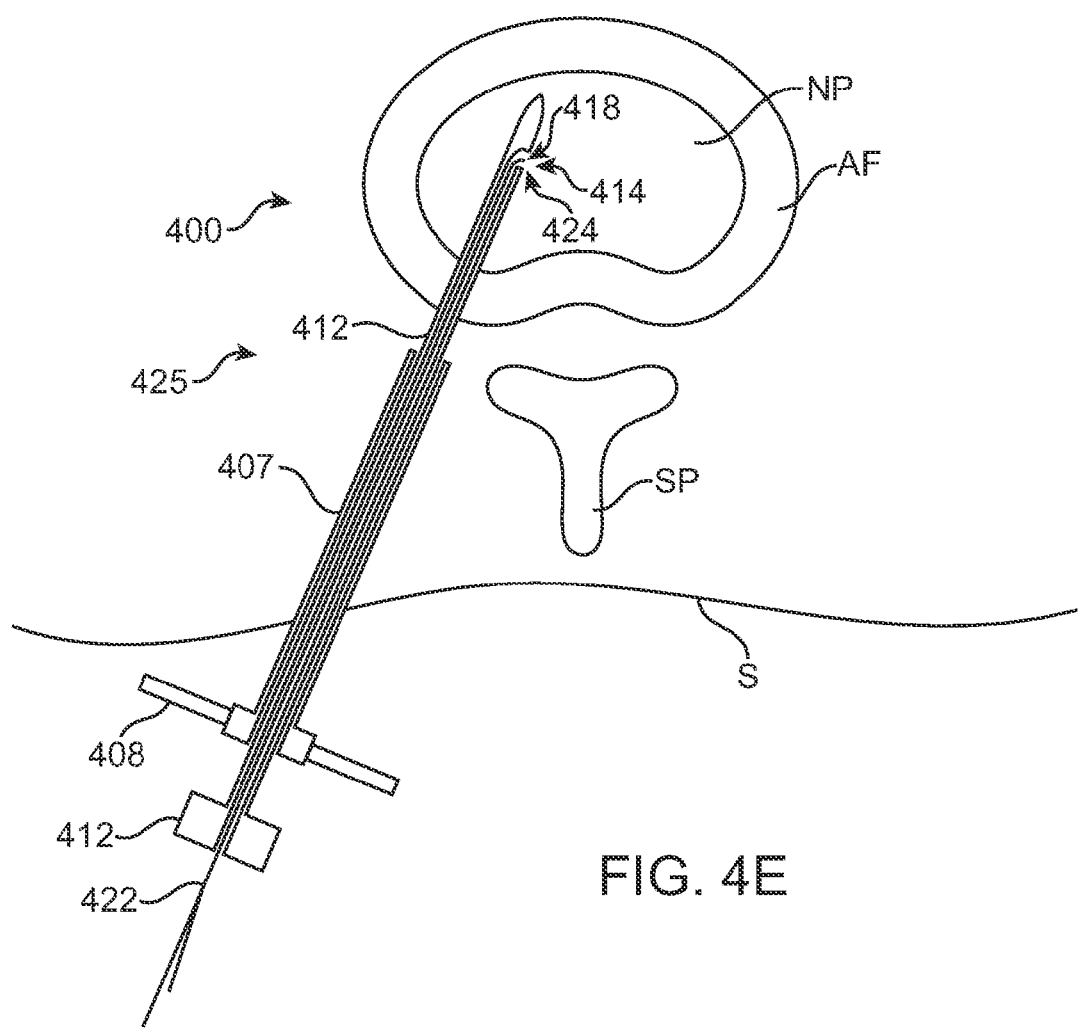
Figure 4F:
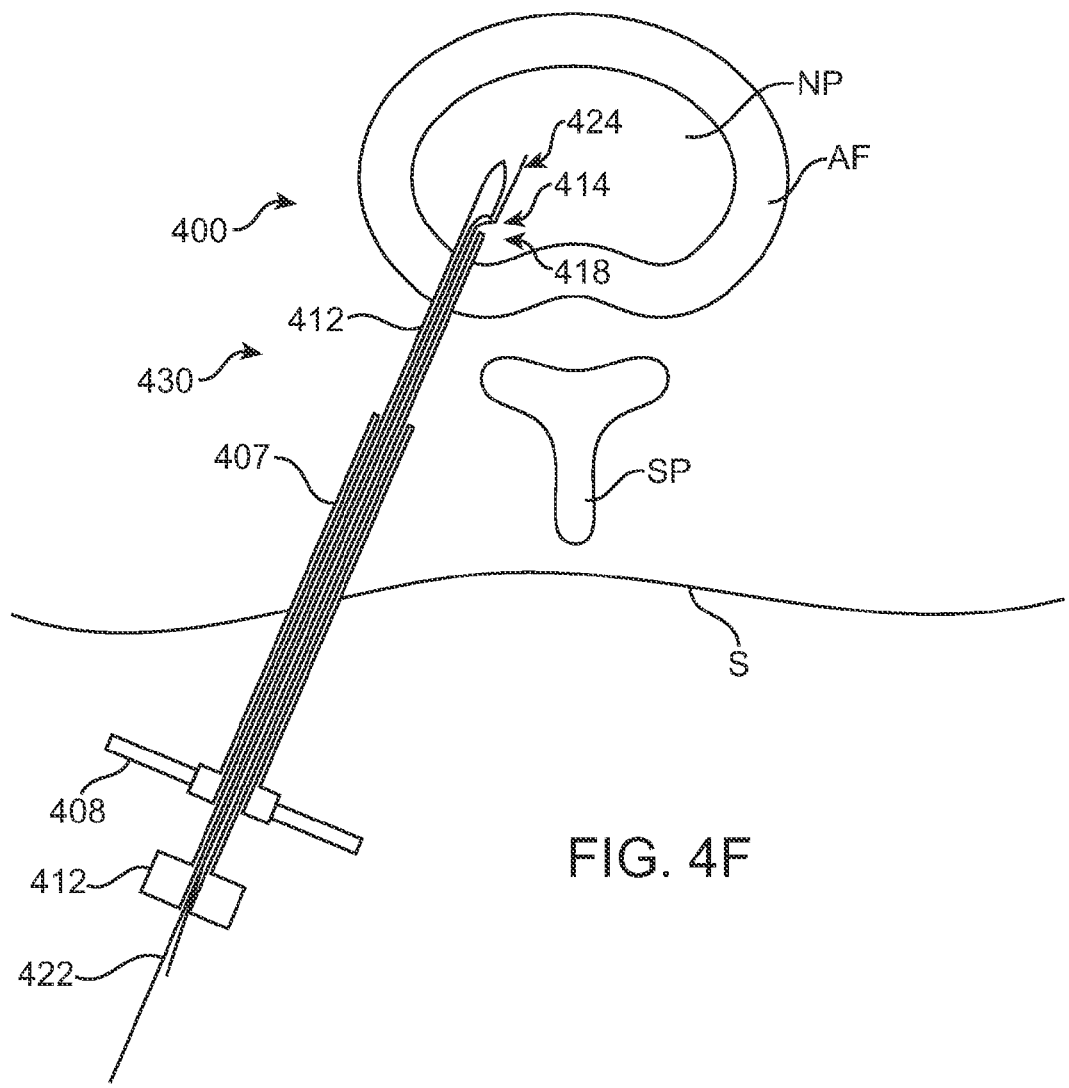
Figure 4G:
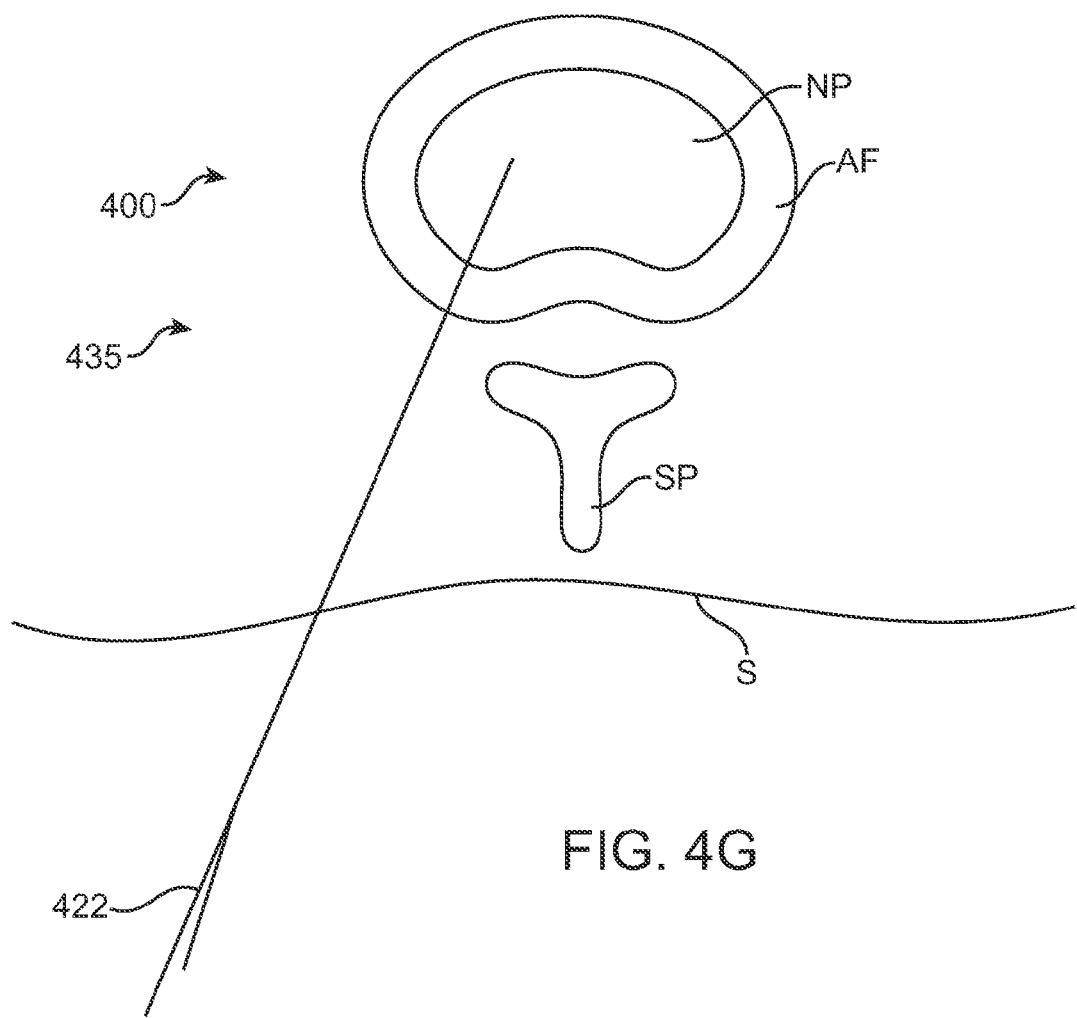
Figure 4H:
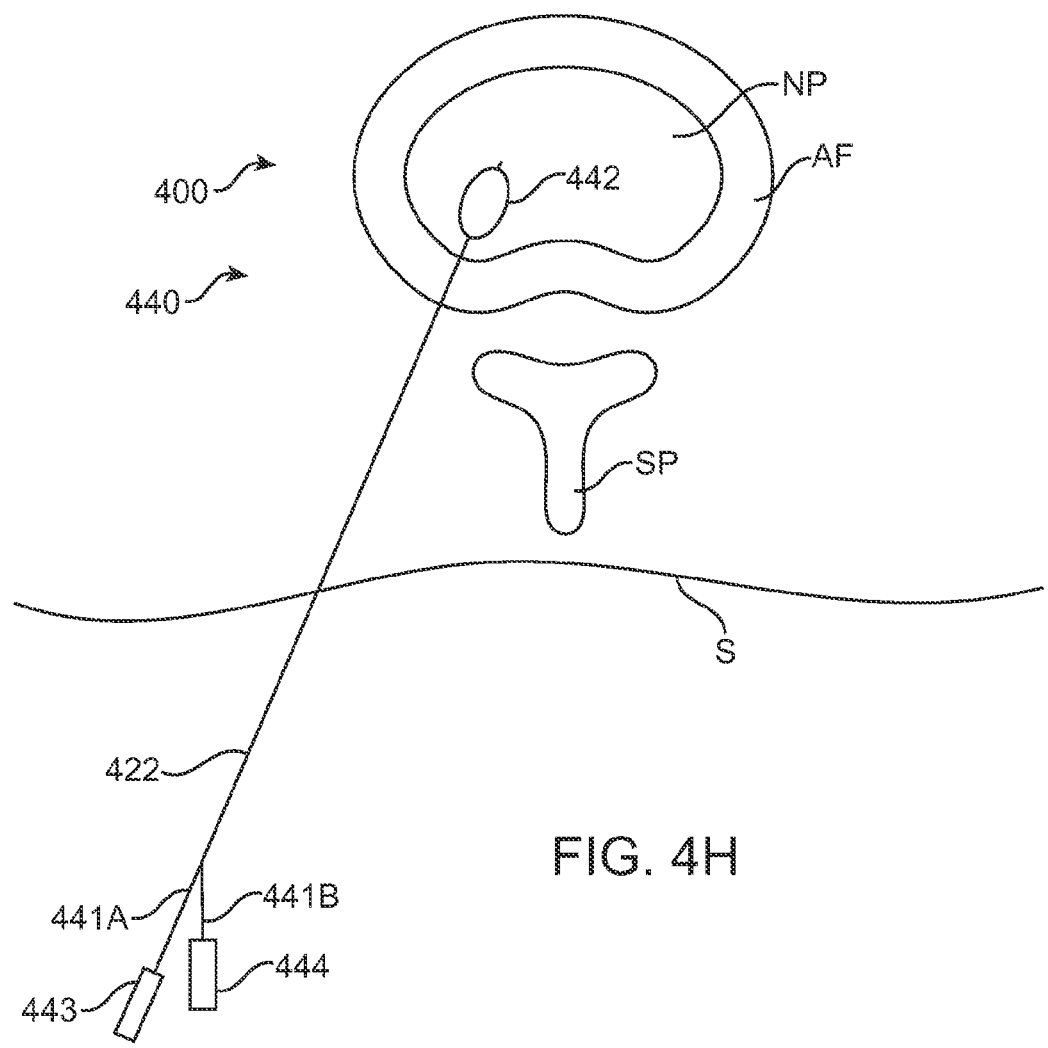
Figure 4I:
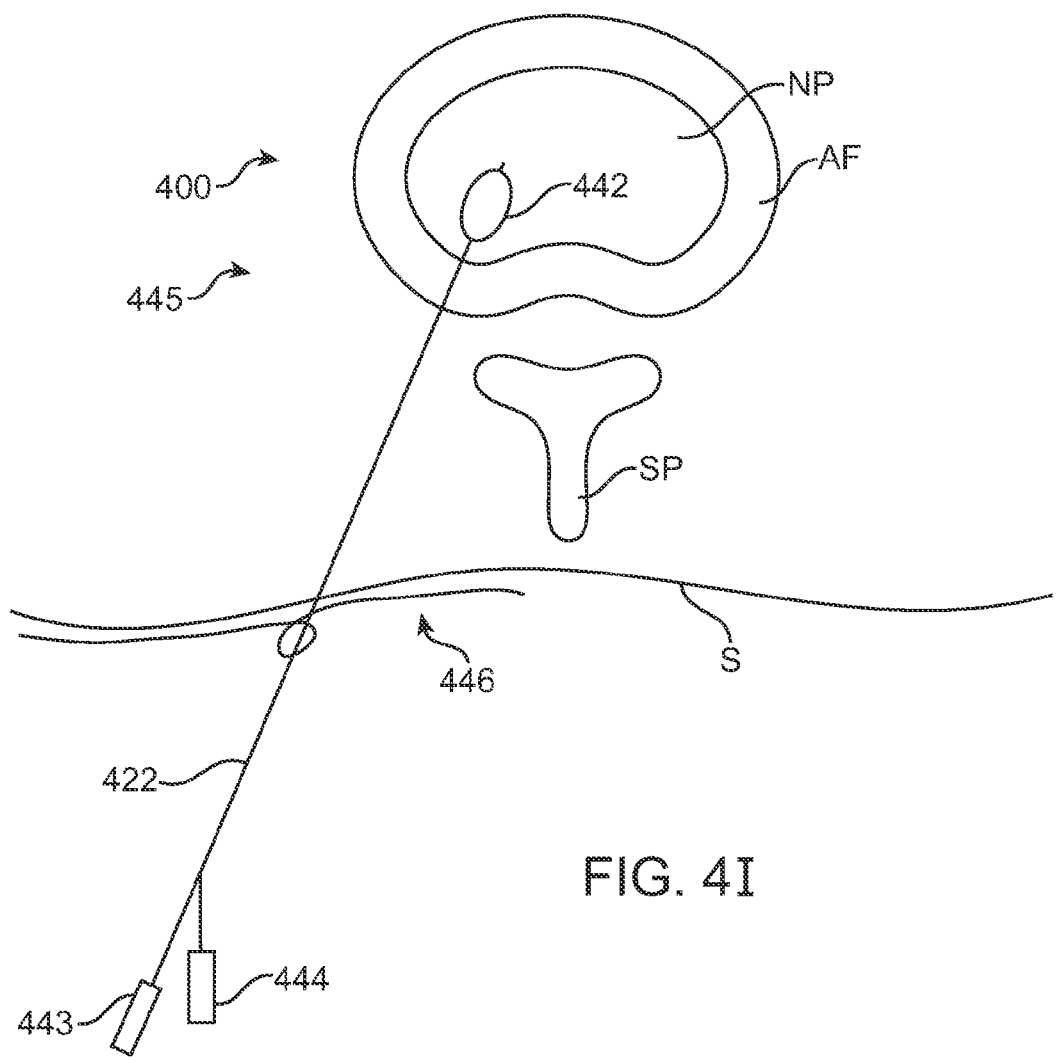
Figure 4J:
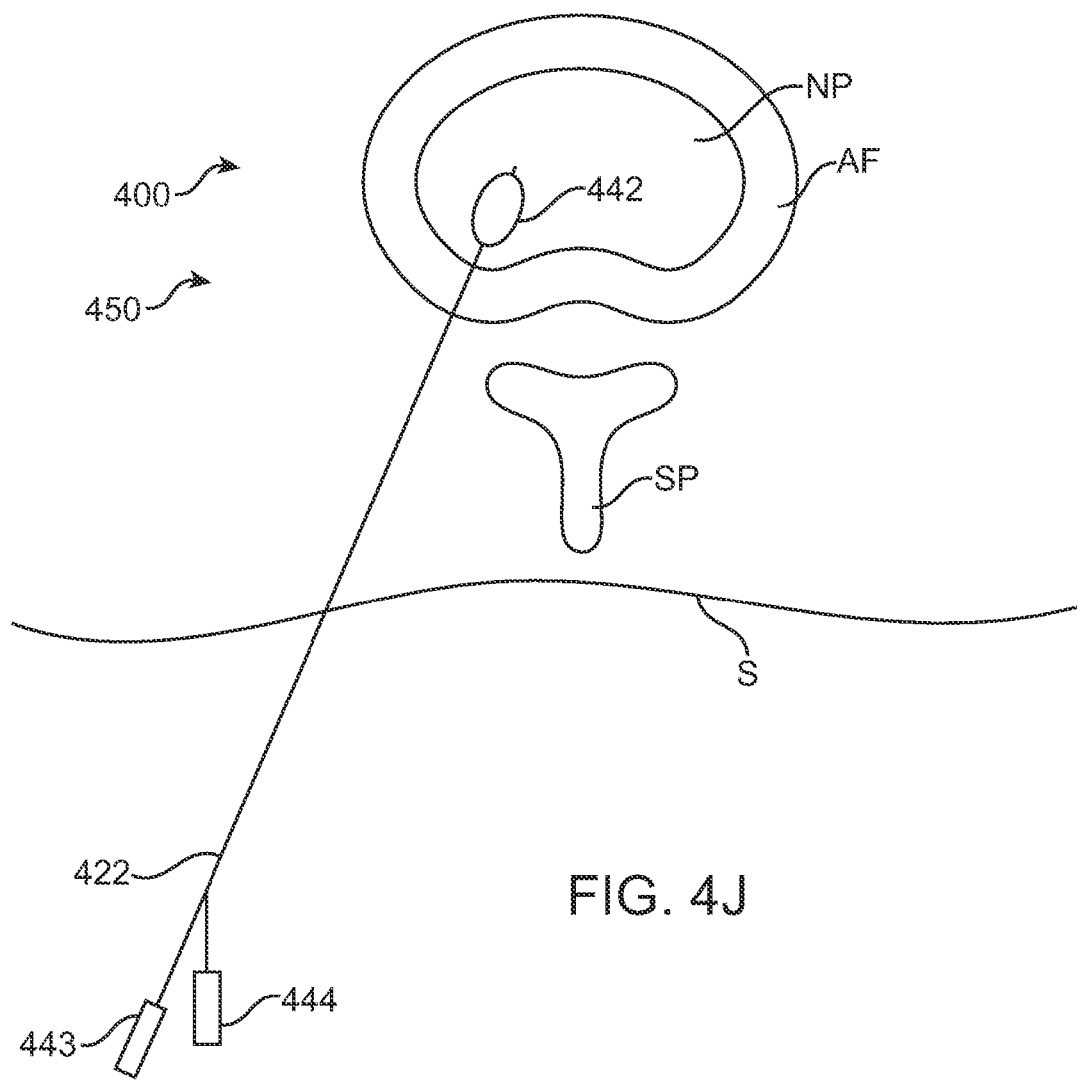

Referring now to FIG. 3I, a coating 392 is shown on inflation tube 331 and a coating 394 is shown on injection tube 351 of catheter 310, according to embodiments of the present invention. During the functional testing portion of the test, the FAD catheter can be secured to the patient, and the patient can be asked to perform activities that provoke typical and/or representative pain for the patient. During these activities it is possible that the proximal ends of the tubes could be repeatedly bent. If these tubes are excessively deformed, it is possible that the tube material could fatigue and break. If the injection tube breaks, injections may no longer be possible. If the balloon tube breaks the balloon may lose inflation pressure, possibly allowing the catheter tip to migrate from the disc space. The inflation and/or injection tubes can be reinforced with coatings to prevent fracture, and in some embodiments to maintain integrity of the tubes after the tubes fracture. Coating 392 and/or coating 394 may comprise PEEK, PET and/or other polymers known in the art. These coatings can increase rigidity of the tubes so as to decrease the possibility of fracture. In some embodiments, the tubes, for example the inflation tube, can be coated with the polymer such that the coating can withstand high presser after the tube fractures and the fluid does not leak through the coating and is retained by the coating. The polymer coating may be attached with adhesive, melted to the tube and/or can be made of a heat shrink material that is shrunk onto the tube.

As noted above, the proximal ends of the tubes may be exposed to repeated stresses that may potentially cause the tubes to fracture from fatigue. In some embodiments, the inflation and injection tubes may comprise heat treated metal and/or metal alloy. In specific embodiments, the tubes may comprise stainless steel tubes that can be supplied in a fully hardened treatment state. Although fully hardened stainless steel can be stiff, strong, and fairly elastic, such stainless steel can have a moderate resistance to fatigue loading. In some embodiments, the tubes can be fully and/or partially annealed to improve the fatigue characteristics. Specific embodiments may comprise partially and/or fully annealed tubes, for example selectively annealed tubes. Such embodiments may comprise a distal portion of the tube that is fully hardened and a proximal portion of the tube outside the patient that is annealed.

Referring now to FIGS. 4A to 4J, a method 500 of delivering a catheter is shown that uses an atraumatic inner needle comprising a side port, according to embodiments of the present invention. A step 405 positions an outer needle 407, or introducer needle. Outer needle 407 many comprise wings 408 to facilitate handling. Outer needle 407 can be passed through a skin S with a stylet 409 positioned inside outer needle 407, such that outer needle 407 and stylet 409 are positioned near spinal process SP and outside annulus fibrosis AF and nucleus pulposus NP. In some embodiments, stylet 409 may comprise an obturator, that can obstruct a hole such as the lumen of outer needle 407 which protrudes through the distal opening of the outer needle 407. The obturator may comprise an atraumatic rounded and/or blunt tip with a sharp point, as described above, so as to penetrate tissue with minimal cutting and/or trauma. Stylet 409 can then removed from outer needle 407. A step 410 passes an inner needle 412 through outer needle 407, such that a distal tip of inner needle 412 can be advanced into the interior of the disc space, for example into nucleus pulposus NP. In some embodiments, inner needle 412 comprises a Special Sprotte needle with a blunt atraumatic tip and side port, as described above. A step 415 may perform a traditional provocative discography, and then flush inner needle 412 with saline. The traditional discography may comprise injection of a substance 416, for example a contrast agent as described above, through inner needle 412. A step 420 delivers a catheter 422 to a side port distal opening 414 of inner needle 412. Catheter 422 may comprise a distal radiopaque marker, as described above. Catheter 422 may comprise depth coding, for example color coding, as described above. Inner needle 412 may comprise a hub 416. Color and/or color changes on catheter 422 near inner hub 416 can indicate a position of a distal tip of the catheter in relation to the inner needle opening and/or spinal disc, as described above. A step 425 advances a distal end 424 of catheter 422 just past a ramp 418 near side port 414 of inner needle 412. A step 430 removes both inner needle 407 and outer needle 412 simultaneously, for example using over the wire technique, such that distal end 424 of catheter 422 remains near the interior of the disc. The distal portion of catheter 422 that comprises the radiopaque marker and balloon can be adapted to slide along ramp 418 and through side port 418 while the inner needle and outer needle are retracted proximally, such that the catheter tip remains near the interior of the disc. A step 435 fully retracts outer needle 407 and inner needle 412 proximally such that catheter 422 remains in place in the interior of the disc and the inner and outer needle are removed from skin S of the patient. A step 440 attaches a Tuohy Borst adapter 443 and a Tuohy Borst adapter 444, and inflates a balloon 442. Adapter 443 can be connected to an injection lumen 441A, as described above. Adapter 444 can be connected to an inflation lumen, as described above. In some embodiments, step 440 can be facilitated. For example, some components can be packaged assembled such that the components are removed from a kit in a pre-assembled configuration. Injection lumen 441A can be connected to a pre-assembled check valve and/or wing nut with adapter 443. The wing nut can with adapter 443 can be color coded to injection lumen 441A. Inflation lumen 441B can be connected to a pre-assembled wing nut, pressure relief valve and/or stop cock with adapter 444. The wing nut with adapter 444 can be color coded to inflation lumen 441B. Such coding can be explained in the instructions for use. A step 445 can tie down catheter 422 with tie down 446, for example an Epi-Guard tie down and/or custom tie downs, known in the art and commercially available from Lina Medical of Copenhagen, Denmark and Dyna Medical Corporation of Ontario, Canada. A step 450 performs a functional test on the patient. The functional test may include many known functional techniques, including having the patient assume a painful position and injecting a substance, as described above, into the disc to identify the disc as a source of pain in response to the patient reaction to the injected substance.

It should be appreciated that the specific steps illustrated in FIGS. 4A to 4J provide a particular method of accessing the interior of an intervertebral disc, according to an embodiment of the present invention. Other sequences of steps may also be performed according to alternative embodiments. For example, alternative embodiments of the present invention may perform the steps outlined above in a different order. Moreover, the individual steps illustrated in FIGS. 4A to 4J may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 5:
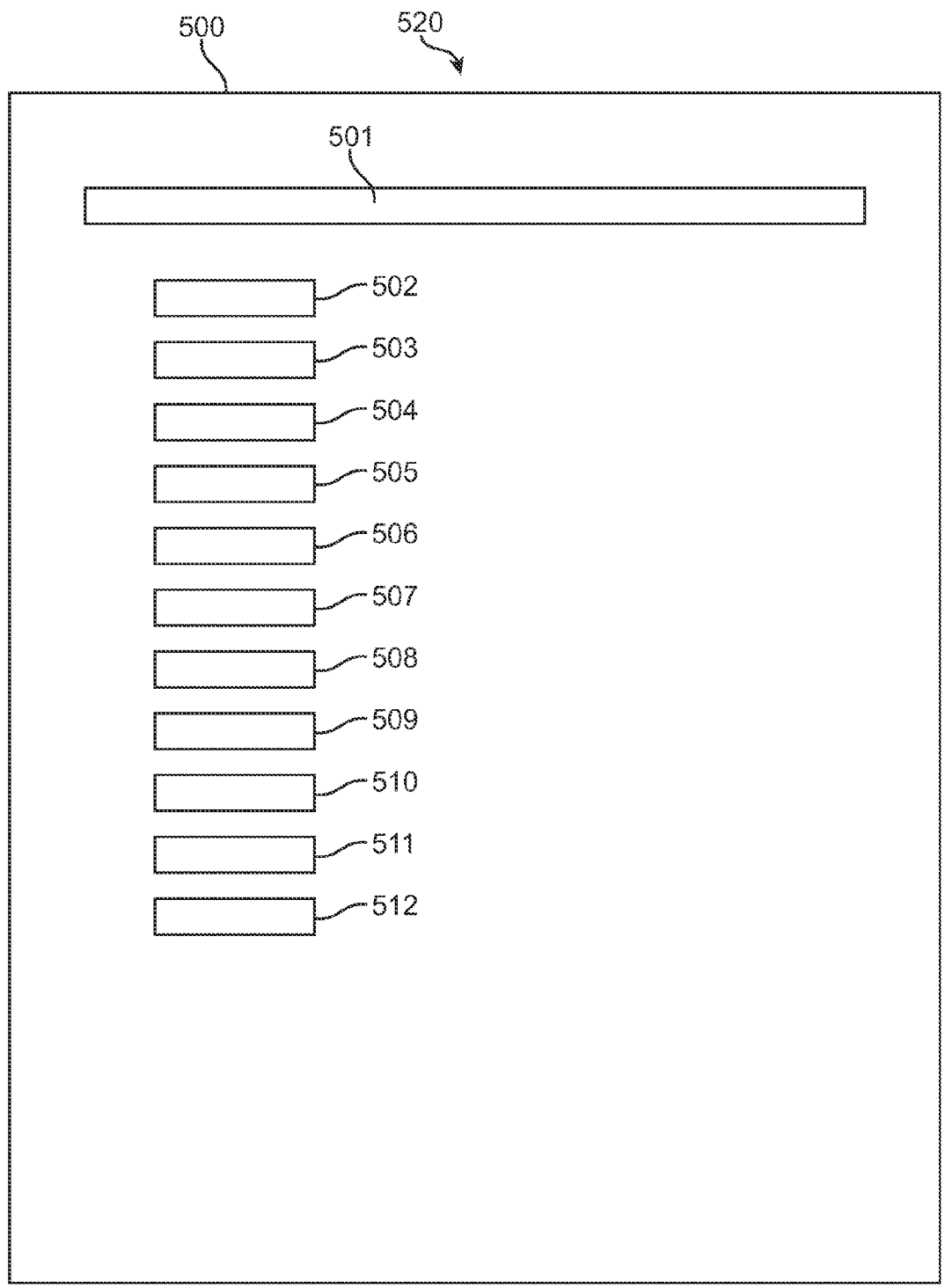
FIG. 5 schematically illustrates a kit, according to embodiments of the present invention.

Referring now to FIG. 5, components of a kit 500 are shown, according to embodiments of the present invention. A Functional Anesthetic Discography Procedure may use a system 520 that comprises the components of kit 500. Such components can be used to deliver radiopaque contrast, local anesthetics, and/or saline solution to the intradiscal space, the dosage amounts can vary may comprise a single dose or continuous administration.

Components of kit 500 may comprise: a catheter 501; a 1.2 mm (18 gauge) Discyphor Direct™ Outer Needle 502 with wing; a 0.9 mm (20 gauge) Discyphor Direct™ Inner Needle 503; a stopcock (one-way) 504; a 3 cc syringe with a pressure relief valve 505; two 1 cc syringes 506; two Touhy-Borst 507; two Touhy-Borst Tie-Downs 508; two wing nuts 509; a Catheter Tie-Down (Epi-Guard) 510; a package of sterile labels 511; and instructions for use (IFU) 512. At least some of the components of kit 500 are commercially available from Kyphon, Inc. of Sunnyvale, Calif. Catheter 501 may comprise many of the catheters described above, for example catheters that can be delivered through a side port of an atraumatic needle. The 1.2 mm outer needle 502 with wing may comprise an outer needle, as described above. The 0.9 mm inner needle 503 many comprise inner needles described above, for example a special Sprotte Needle as described above. Stopcock (one-way) 504 may comprise a one-way check valve as described above. The 3 cc syringe with a pressure relief valve 505 may comprise a pressure relieve valve as described above. The two 1 cc syringes 506 may comprise commercially available and known 1 cc syringes. The two Tuohy Borst 507 may comprise known commercially available Tuohy Borst adapters as described above. The two Tuohy Borst Tie-Downs 508 may comprise known commercially available Tuohy Borst Tie Downs. The two wing nuts 509 may comprise injection molded wing nuts, as described above The Catheter Tie-Down (Epi-Guard) 510 may comprise a known commercially available tie-down as described above. The package of sterile labels 511 may comprise known commercially available sterile labels. Instructions for use (IFU) 512 may comprises printed and/or other instructions with figures that show how to use the components of kit 500.

In some embodiments, components of the kit, or system, can be sold separately. For example, the inner and outer needle can be provided "a la carte" and separate from other components, such that the inner and outer needle are provided together as a pair comprised within a sterile package. In specific embodiments, a 89 mm (3.5") long by 1.2 mm (18 g) outer needle can be provided with a 178 mm (7") long by 0.9 mm (20 g) wide inner needle in a sterile package. In a specific embodiment a 127 mm (5") long by 0.9 mm (18 g) wide outer needle can be provided with a 203 mm (8") long by 0.9 mm (20 g) wide inner needle in a sterile package.

Many of the above metal structures, for example stylets, tubes, guidewires and radiopaque coils, may comprise the following advanced metals and alloys thereof: tungsten, rhenium, molybdenum, tantalum and palladium. In specific embodiments, the structures comprise at least one of the following advanced metal alloys: tungsten-rhenium, tungsten-carbide and molybdenum-rhenium. In specific embodiments, the above structures comprise cobalt-chromium, for example a cobalt-chromium-nickel commercially available and known as Elgiloy™. Work in relation to embodiments of the present invention indicates that structures comprising tungsten-rhenium, tungsten carbide, molybdenum-rhenium and pure rhenium can provide much stiffer, stronger and radiopaque stylets, tubes, guidewires and radiopaque coils than for example a Super Stiff Amplatz guidewire. Material parameters that can benefit from such advanced metals and alloys include overall strength, radiopacity, tensile strength, axial strength, stiffness, elongation at break, modulus of elasticity, Poisson's ratio, shear modulus, electrical resistivity, magnetic susceptibility, specific heat capacity, or thermal conductivity. Such advanced metals and metal alloys can provide reduced catheter sized, with greater pushability, radiopacity, and overall strength, thereby providing smaller, easier to use and less invasive devices. In some embodiments, needles and stylets comprising such advanced metals and advanced alloys may comprise thinner needle and stylet walls that can penetrate tissue with less needle force, can provide more pushability, strength and memory than, for example, a stainless steel needle or stylet. Known metallurgy techniques, for example annealing, can be used to treat the advanced metals and metal alloys to provide the desired material properties.

In some embodiments, the advanced metal or advanced metal alloys can be used in many interventional fields such as orthopedics, GI, peripheral, cardiovascular, neurovascular, and other percutaneous procedures, for example those in which catheters are used with active strengthening wires. In a specific embodiment, the advanced metals and advanced metal alloys can be used with endoscopic retrograde cholangio-pancretography (ERCP). With ERCP catheter size can be very important when cannulating the Sphincter of Oddi (Major Papilla) and accessing body lumens such as the bile or pancreatic duct. In some embodiments, the advanced metal and metal alloys can be used to reinforce a catheter body and/or other structures so as to alleviate kinking and/or bending that may arise at the elevator of an endoscope, for example with an ERCP catheter. In some embodiments, the advanced metal and/or metal alloys can be used with medical device implants, for example orthopedic implants such as pedicle screws, rods, and cages. In specific embodiments, embolism coils may comprise the advanced metals and metal alloys described above to provide significant radiopacity.

Figure 6A:
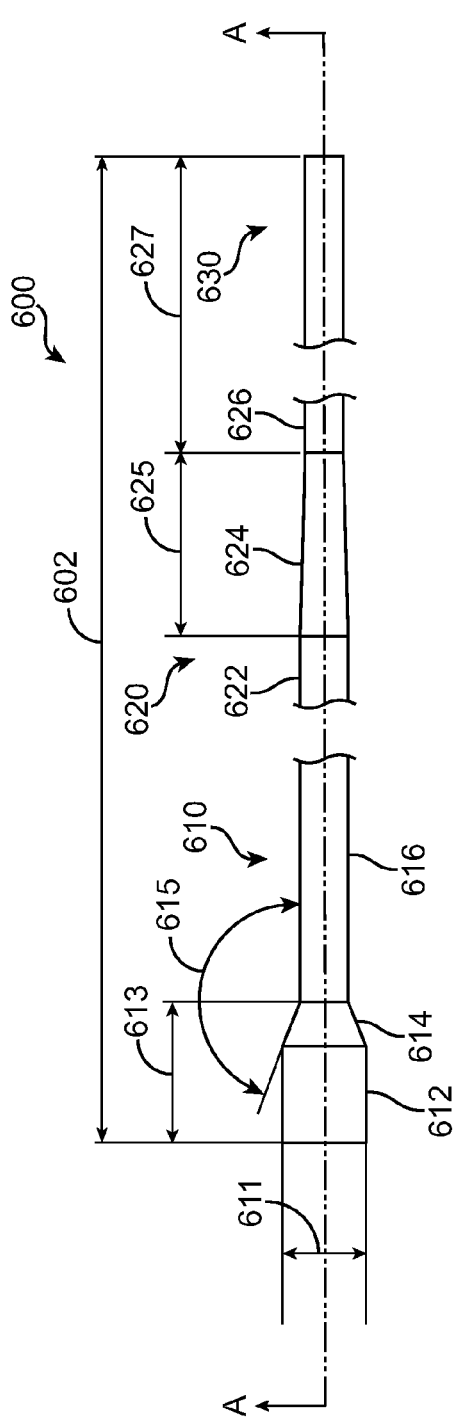
FIGS. 6A and 6B schematically illustrate, a tapered inner needle, according to embodiments of the present invention.
Figure 6B:
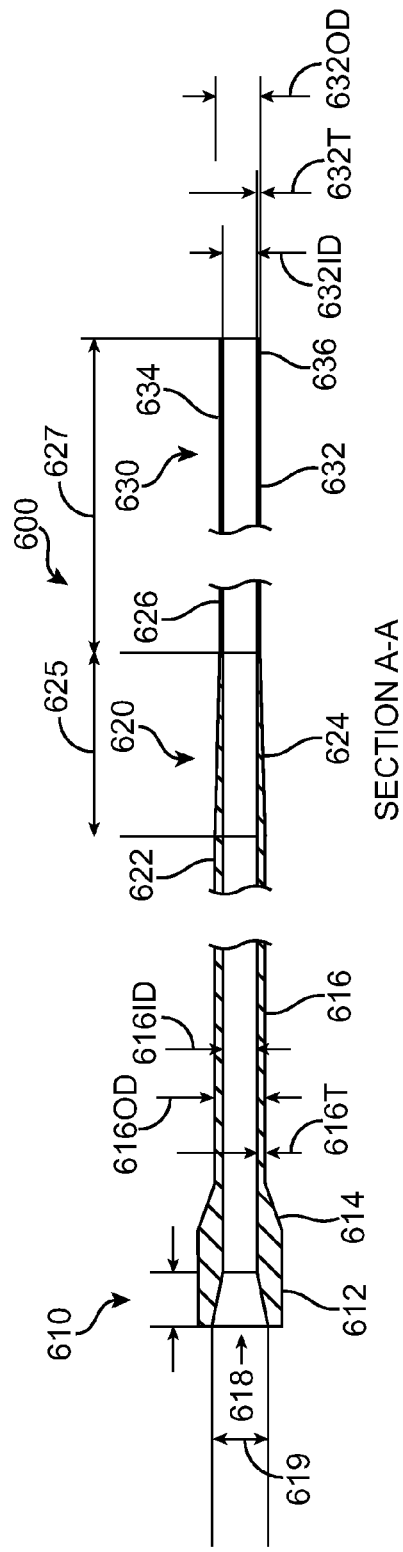

Referring now to FIGS. 6A and 6B, a tapered inner needle 600 is shown, according to embodiments of the present invention. Inner needle 600 can be sized to pass through a lumen of the outer needle and may comprise an inner needle stylet, as described above. In many embodiments, tapered inner needle comprises a tapered outside diameter along the needle shaft while the inside diameter remains substantially constant. Inner needle 600 comprises a proximal portion 610, a tapered middle portion 620, a distal portion 630, and a length 602. In between the proximal end and distal end, inner needle 600 can be sized to fit within the outer needle. The inner needle can comprise proximal dimensions sufficient for stiffness and distal dimensions to penetrate the annulus with minimal trauma. For example, middle portion 620 may comprise a tapered middle section 622 that extends beyond the outer needle when then the inner needled is placed. This taper permits the distal portion of the inner needle to be thin so as to minimize tissue damage and permits the proximal portion to be thicker and provide stiffness. Inner needle 600 may comprise thin walled tubes made from known polymers such as PEEK, polyimide (e.g. Ultem™, polyether imide), poly carbonate, polyetherimide (PEI, Ultem®), polyphenylsulfone (PPSU, Radel R®), Acetal (POM, Delrin®), PPS (Fortron®, Ryton®), or polyimide (Vespel®) Inner needle 600 may comprise an injection molded needle using known injection molding techniques and materials. Alternatively inner needle 600 may be formed using heat (created with IR/UV/RF/or electrical resistance) and formed from extrusion(s) using known forming techniques and materials. In some embodiments, the injection molded needle may comprise an atraumatic tip with side port and ramp, as described above. In some embodiments, the tapered needle may comprise stainless steel. However, work in relation with the present invention suggests the polymer inner needle can be less brittle than comparable thin walled stainless steel tubes, and the polymer inner needle may require more cycles and/or force to break than the stainless steel needle tube, even after the polymer needle has kinked. Such characteristic can be helpful to avoid the unlikely event that such broken needle could break in the patient. In some embodiments, the improved material properties of such polymers permit the design of tapered inner needles with a smaller outside diameters that may cause less trauma to the penetrated disc. Also, known injection molding or folding techniques can make the polymer needle easier to manufacture.

Proximal portion 610 comprises a lug 612 for engaging the needle hub. Lug 612 comprises an outer diameter 611. Proximal portion 610 comprises an incline 614 at an angle to fit engage the hub. A distal section 616 of proximal portion 610 comprises a size to fit within the outer needle, for example an outer diameter 616 OD. A lumen of inner needle 600 comprises an inner diameter 616ID. Distal section 616 of proximal portion 610 comprises a thickness 616T to provide strength and/or stiffness. Proximal portion 610 comprises an opening and lumen sized to receive an inner needle stylet, as described above. The inner needle stylet can stiffen the inner needle. A distance 613 from the proximal end of the needle to the distal section of the proximal portion can be about 2.5 mm, in some embodiments. Outside diameter 616OD can be sized from about 0.7 mm to about 1.1 mm, for example from about 0.889 to about 0.934 mm, and inside diameter 616ID can be from about 0.5 mm to about 0.8 mm, for example from about 0.648 to about 0.712 mm. Thickness 632T can be from about 0.1 mm to about 0.15 mm, for example about 0.127 mm.

Middle portion 620 comprises a proximal section 622, a middle section 624 and a distal section 626. Proximal section 622 may remain inside the outer needle when placed in the patient. Thus proximal section 622 may comprise dimensions similar to the distal section 616 of proximal portion 610 that fit inside the outer needle. Middle section 622 may comprise a taper where the outside diameter of the inner needle becomes smaller distally and the inside diameter remains substantially constant. In many embodiments, middle section 624 extends slightly beyond the outer needle tip when the inner needle is positioned, so as to minimize tissue damage and provide stability. The taper of distal section 624 extends over a distance 625. Distance 625 can be about 2.5 mm (0.1) inches, in some embodiments.

Distal portion 630 comprises a proximal section 632, a middle section 634 and a distal section 636. Distal portion 630 comprises a substantially constant inside diameter, outside diameter and tube thickness that extends along proximal section 632, middle section 634 and distal section 636. Proximal section 632 comprises an inside diameter 632ID, an outside diameter 632OD and a tube thickness 632T. In many embodiments, distal section 626 of middle portion 620 comprises dimensions (e.g. tube thickness, inside diameter and outside diameter) that are substantially similar to distal portion 630. This narrow distal portion of the needle extends over a distance 627. In some embodiments distance 627 can extend from about 29 mm to about 35 mm, for example about 32 mm. In some embodiments, outside diameter 632 OD can be from about 0.6 mm to about 1 mm, for example from about 0.813 mm to about 0.823 mm, and inside diameter 632ID can be from about 0.5 mm to about 0.8 mm, for example from about 0.648 mm to about 0.673 mm. Thickness 632T can be from about 0.05 to about 0.1 mm, for example about 0.076 mm.

In many embodiments, outside diameter 632OD on the distal portion is smaller than outside diameter 616OD on the proximal portion while the inside diameter (e.g. 616ID and 632ID) remains substantially constant, such that thickness 632T on the distal portion is smaller than thickness 616T that fits inside the outer needle.

While the above is a complete description of the preferred embodiments of the present invention, other embodiments may fall within the spirit and scope of the invention. Therefore, the scope of the present invention should be determined with reference to the appended claims along with their full scope of equivalents.

What is claimed is:

1. A catheter for accessing an intervertebral disc, said catheter comprising:
   an elongate flexible catheter body having a proximal portion, a distal portion, and at least one lumen for housing an injection tube and an inflation tube;
   the injection tube extending from the proximal portion to a distal tip of the catheter body, the injection tube being arranged to deliver an injection medium distally beyond an anchoring balloon into an intervertebral disc space;
   an inflatable anchoring balloon on the distal portion of the catheter body;
   an inflation tube extending from the proximal portion to the distal portion of the catheter body;
   an attachment member removably coupled to a proximal portion of the inflation tube, the attachment member having a channel extending from a proximal end to a distal end of the attachment member, the attachment member having a slot opening extending from the proximal end to the distal end in communication with the channel;

a first Tuohy Borst connector removably coupled to the attachment member and the inflation tube;

a stopcock removably coupled to the first Tuohy Borst connector, the stopcock comprising a first pressure relief structure that vents an inflation medium if the pressure exceeds a predetermined pressure;

a first check valve upstream from and removably coupled to the stopcock, the first check valve ensures that the inflation medium only flows downstream in the direction of the stopcock;

a second pressure relief structure removably coupled to the first check valve; and a first syringe removably coupled to the first check valve, wherein the first syringe injects the inflation medium into the first check valve to inflate the inflatable anchoring balloon such that when the inflatable anchoring balloon reaches the predetermined pressure the second pressure relief structure opens and the inflation medium passes through an exit port of the second pressure relief structure in a visible manner such that a user of the catheter knows the predetermined pressure has been reached;

wherein the slot opening permits removal of the attachment member over the inflation tube such that the attachment member can be removed from the inflation tube while the first Tuohy Borst connector remains removably coupled to the inflation tube.

2. A catheter as in claim 1, wherein the second pressure relief structure further comprises a tubular body having an interior surface defining a channel in communication with the first check valve and the stopcock such that the inflation medium injected into the first check valve passes through the channel into the stop cock;

a seal forming a portion of the interior surface of the channel, the seal formed by a spring exerting a second predetermined pressure against a ball causing the ball to sealing interface with a seat; wherein the predetermined pressure is greater than the second predetermined pressure such that the seal is broken and the inflation medium passes through the exit port.

3. A catheter as in claim 1, wherein the attachment member is a first wing nut.

4. A catheter as in claim 1, further comprising:

a second wing nut removably coupled to a proximal portion of the injection tube;

a second Tuohy Borst connector removably coupled to the second wing nut and the injection tube;

a third check valve upstream from and removably coupled to the second Tuohy Borst, the second check valve ensures that the injection medium only flows downstream in the direction of the second Tuohy Borst; and a connector operable to connect to a second syringe that injects the injection medium into the connector.

* * * * *

UNITED STATES PATENT AND TRADEMARK OFFICE
CERTIFICATE OF CORRECTION

| | | |
|---|---|---|
| PATENT NO. | : 8,002,743 B2 | Page 1 of 1 |
| APPLICATION NO. | : 11/764085 | |
| DATED | : August 23, 2011 | |
| INVENTOR(S) | : Miller et al. | |

It is certified that error appears in the above-identified patent and that said Letters Patent is hereby corrected as shown below:

In Column 1, Line 62, delete "more that" and insert -- more than --, therefor.

In Column 13, Line 2, delete "antiinflammatory" and insert -- anti-inflammatory --, therefor.

In Column 13, Line 6, delete "tissue gragments;" and insert -- tissue fragments; --, therefor.

In Column 13, Line 9, delete "thereof," and insert -- thereof; --, therefor.

In Column 13, Line 13, delete "thereof," and insert -- thereof; --, therefor.

In Column 13, Line 19, delete "thereof," and insert -- thereof; --, therefor.

In Column 14, Line 41, delete "Whittacre" and insert -- Whitacre --, therefor.

In Column 23, Line 33, delete "(Vespel ®)" and insert -- (Vespel ®). --, therefor.

Signed and Sealed this
Twenty-ninth Day of November, 2011

David J. Kappos
*Director of the United States Patent and Trademark Office*